US007939082B2

(12) United States Patent
Frazer et al.

(10) Patent No.: US 7,939,082 B2
(45) Date of Patent: *May 10, 2011

(54) PAPILLOMA VIRUS VACCINE

(75) Inventors: Ian Frazer, Brisbane (AU); Jian Zhou, Brisbane (AU)

(73) Assignees: The University of Queensland, St. Lucia, Queensland (AU); CSL Limited, Parkville, Victoria (AU)

( * ) Notice: Subject to any disclaimer, the term of this patent is extended or adjusted under 35 U.S.C. 154(b) by 378 days.

This patent is subject to a terminal disclaimer.

(21) Appl. No.: 12/318,138

(22) Filed: Dec. 22, 2008

(65) Prior Publication Data

US 2009/0252761 A1 Oct. 8, 2009

Related U.S. Application Data

(60) Continuation of application No. 11/455,236, filed on Jun. 19, 2006, now abandoned, which is a division of application No. 08/185,928, filed as application No. PCT/AU92/00364 on Jul. 20, 1992, now Pat. No. 7,476,389.

(30) Foreign Application Priority Data

Jul. 19, 1991 (AU) ...................................... PK7322

(51) Int. Cl.
*A61K 39/12* (2006.01)
*C12N 7/00* (2006.01)
*C07K 14/025* (2006.01)

(52) U.S. Cl. .................... 424/204.1; 435/235.1; 530/350

(58) Field of Classification Search .......................... None
See application file for complete search history.

(56) References Cited

U.S. PATENT DOCUMENTS

| 4,551,270 | A  | 11/1985 | Danos et al.   |
|-----------|----|---------|----------------|
| 5,045,447 | A  | 9/1991  | Minson         |
| 5,071,757 | A  | 12/1991 | Kreider et al. |
| 5,437,951 | A  | 8/1995  | Lowy et al.    |
| 6,613,557 | B1 | 9/2003  | Frazer et al.  |
| 7,169,585 | B2 | 1/2007  | Frazer et al.  |
| 7,476,389 | B1 | 1/2009  | Frazer et al.  |

FOREIGN PATENT DOCUMENTS

| WO | WO 91/04330  | 4/1991  |
|----|--------------|---------|
| WO | WO 92/16638  | 10/1992 |
| WO | WO 93/02184  | 2/1993  |
| WO | WO 94/00152  | 1/1994  |
| WO | WO 94/05792  | 3/1994  |
| WO | WO 94/20137  | 9/1994  |

OTHER PUBLICATIONS

Summers et al., "A Manual of Methods for Baculovirus Vectors and Insect Cell Culture Procedures," Texas Agricultural Experiment Station Bulletin No. 1555 (1987).

Zhou et al., "Increased Expression of Vaccinia Recombinant HVP 16 L1 and L2 ORF Proteins in Epithelial Cells is Sufficient for Assembly of HPV Virion Like Particles," J. Gen. Virology, 1990, pp. 2185-2190, vol. 71.
Zhou et al., "Increased antibody responses to human papillomavirus type 16 L1 protein expressed by Recombinant vaccine virus lacking serine protease inhibitor genes," Chemical Abstracts, Nov. 5, 1990, vol. 13, No. 19.
Zhou et al., "Human Papillomavirus Type 16 Virions Produced by a Recombinant Vaccinia Virus" Abstract from 1991 Papillomavirus Workshop (Seattle, WA 1991).
Zhou et al., "Definition of Linear Antigenic Regions of the HPV 16 L1 Capsid Protein Using Synthetic Virion-like Particles" *Virology*, 189:592-599 (1992).
Article entitled *Increased Antibody Responses to Human Papillomavirus Type 16 L1 Protein Expressed by Recombinant Vaccina Virus Lacking Serine Protease Inhibitor Genes*, from Chemical Abstract, vol. 13, No. 19, issued Nov., (1990).
International Search Report for PCT/AU92/00364, (1992).
Article entitled *Expression of Vaccinia Recombinant HPV 16 L1 and L2 ORF Proteins in Epithelial Cells is Sufficient for Assembly of HPV Virion-Like Particles*, from Virology, vol. 185, No. 1, 1991.
International Application PCT/NL90/00130 filed Sep. 11, 1990 by Rijksuniversiteit Te Leiden.
Galloway, Journal of the National Cancer Institute, 86:474-475, (1994).
Tomita et al., *Journal of Virology*, 61:2389-2394, 1987.
Icenogle et al., *Virology*, 184:101-107, Sep. 1991.
Chen et al., *Journal of General Virology*, 79:2137-2146, 1998.
Zhou et al., *Virology*, 185(1): 251-257, 1991.
Office Action dated Jun. 26, 2008 by the Examiner in U.S. Appl. No. 11/455,236 (US 2007/0154902).
Baker, "Sequence Analysis of Papillomavirus Genomes" *The Papovaviridae*, vol. 2—The Papillomaviruses, Salzman and Howley, Eds., Plenum Press (1987).
Baker et al., "Structures of bovine and human papillomaviruses" *Biophys. J.*, 60:1445-1465 (1991).
Browne et al., "Analysis of the L1 Gene Product of Human Papillomavirus Type 16 by Expression in a Vaccinia Virus Recombinant" *J. Gen. Virol.*, 69:1263:1273 (1988).
Carter et al., "Expression of Human Papillomavirus Proteins in Yeast *Saccharomyces cerevisiae*" Virology, 182:513-521 (1991).
Cole et al., "Nucleotide Sequence and Comparative Analysis of the Human Papillomavirus Type 18 Genome," *J. Mol. Biol.*, 193:599-608 (1987).

(Continued)

*Primary Examiner* — Mary E Mosher
(74) *Attorney, Agent, or Firm* — Foley & Lardner LLP

(57) ABSTRACT

A method of providing papilloma virus like particles which may be used for diagnostic purposes or for incorporation in a vaccine for use in relation to infections caused by papilloma virus. The method includes an initial step of constructing one or more recombinant DNA molecules which each encode papilloma virus L1 protein or a combination of papilloma virus L1 protein and papilloma virus L2 protein followed by a further step of transfecting a suitable host cell with one or more of the recombinant DNA molecules so that virus like particles (VLPs) are produced within the cell after expression of the L1 or combination of L1 and L2 proteins. The VLPs are also claimed per se as well as vaccines incorporating the VLPs.

30 Claims, 18 Drawing Sheets

OTHER PUBLICATIONS

Finch et al., "The Structure of Viruses of the Papilloma-Polyoma Type," *J. Mol. Biol.*, 13:1-12 (1965).

Galloway, *Journal Of The National Cancer Institute*, 1994, pp. 474-475, vol. 86, No. 7.

Kirnbauer et al., "Papillomavirus L1 major capsid protein self-assembles into virus-like particles that are highly immunogenic" *Proc. Natl. Acad. Sci. USA*, 89:12180-12184 (1992).

Kirnbauer et al., "Efficient Self-Assembly of Human Papillomavirus Type 16 L1 and L1-L2 into Virus-Like Particles" *J. Virology*, 67:6929-6936 (1993).

Rose et al., "Expression of the full-length products of the human papillomavirus type 6b (HPV-6b) and HPV-11 L2 open reading frames by recombinant baculovirus, and antigenic comparisons with HPV-11 whole virus particles" *J. Gen. Virology*, 71:2725-2729 (1990).

Sambrook et al., Molecular Cloning: A Laboratory Manual, $2^{nd}$ ed., Cold Spring Harbor Laboratory Press (1989).

Seedorf et al., "Human Papillomavirus Type 16 DNA Sequence" *Virology*, 145:181-185 (1985).

Sterling et al., "Production of Human Papillomavirus Type 16 Virions in a Keratinocyte Cell Line" *J. Virology*, 64:6305-6307 (1990).

Office Action issued Jun. 26, 2008, in U.S. Appl. No. 11/455,236, 10 pages.

FIG 2A

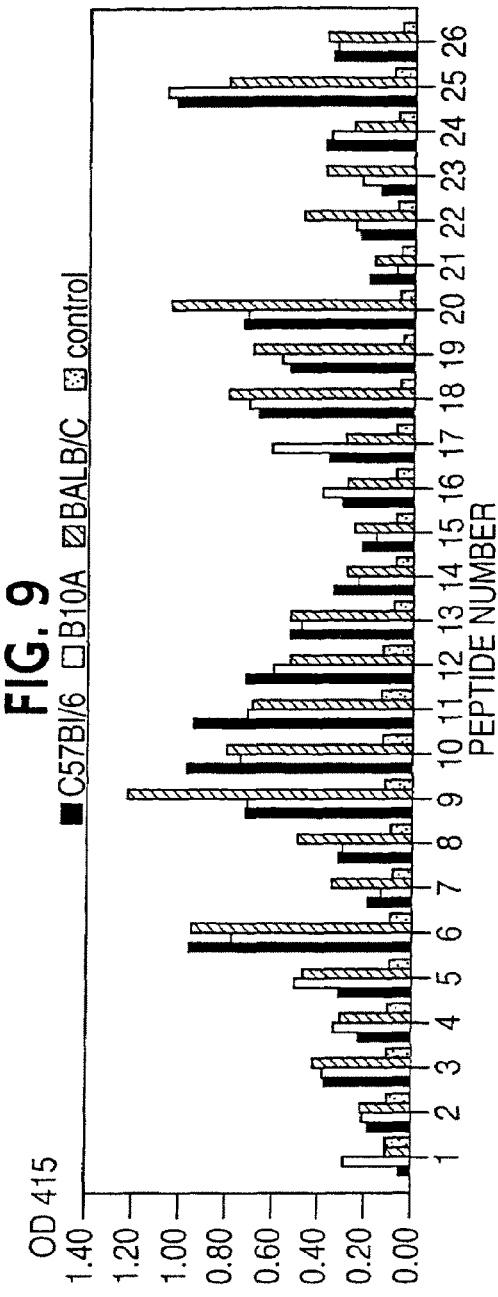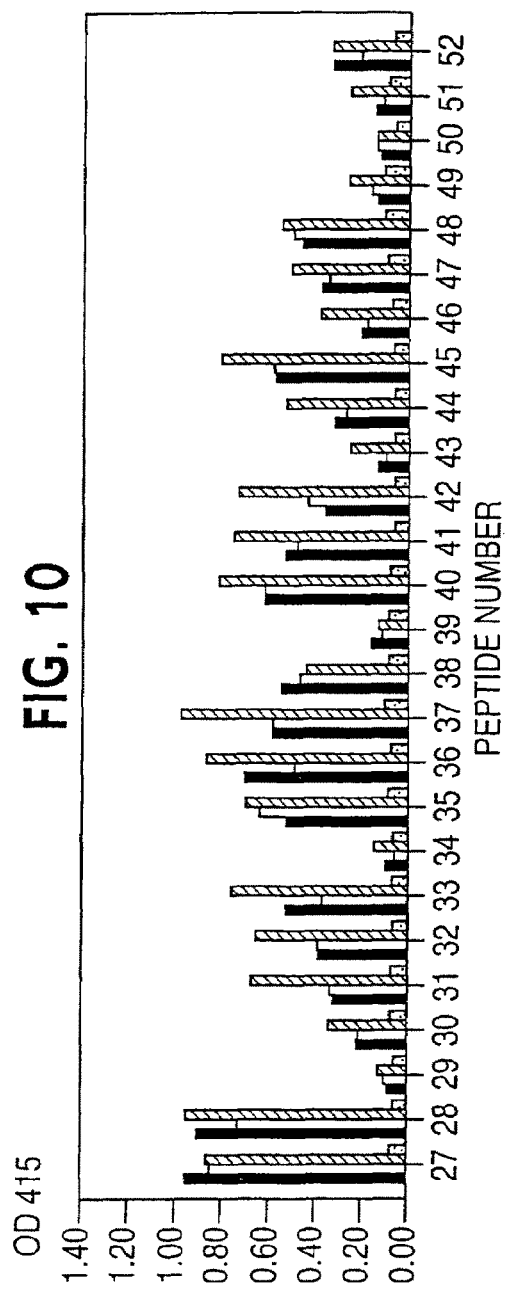

PAPILLOMA VIRUS VACCINE

CROSS-REFERENCE TO RELATED APPLICATIONS

This application is a Divisional of U.S. application Ser. No. 08/185,928, filed Jan. 19, 1994, incorporated herein by reference in its entirety, which is a U.S. National Stage of International Application PCT/AU1992/000364, filed Jul. 20, 1992, incorporated herein by reference in its entirety, which claims benefit of priority to Australian Application PK7322, filed Jul. 19, 1991, incorporated herein by reference in its entirety.

FIELD OF INVENTION

THIS INVENTION relates to papilloma viruses and in particular antigens and vaccines that may be effective in treatment of infections caused by such viruses.

BACKGROUND OF THE INVENTION

Papilloma virus infections are known not only in humans but also in animals such as sheep, dogs, cattle, coyotes, wolves, possums, deer, antelope, beaver, turtles, bears, lizards, monkeys, chimpanzees, giraffes, impala, elephants, whales, cats, pigs, gerbils, elks, yaks, dolphins, parrots, goats, rhinoceros, camels, lemmings, chamois, skunks, Tasmanian devils, badgers, lemurs, caribou, armadillo, newts and snakes (see for example "Papilloma Virus Infections in Animals" by J P Sundberg which is described in Papilloma viruses and Human Disease, edited by K Syrjanen, L Gissman and L G Ross, Springer Verlag 1987).

It is also known (eg. In Papilloma viruses and Human Cancer edited by H Pfister and published by CRC Press Inc 1990) that papilloma viruses are included in several distinct groups such as human papilloma viruses (HPV) which are differentiated into types 1-56 depending upon DNA sequence homology. A clinicopathological grouping of HPV and the malignant potential of the lesions with which they are most frequently associated may be separated as follows.

In a first group may be listed types 1 and 4 which cause benign plantar warts, types 2, 26, 28 and 29 which cause benign common warts, Types 3, 10 and 27 which cause benign flat warts and Type 7 which causes butcher's warts. This first group of infections occur in normal or immunocompetent individuals.

In a second group which refer to immunocompromised individuals there may be listed Types 5 and 8 which cause highly malignant macular lesions, Types 9, 12, 14, 15, 17, 19-25, 36 and 46-50 which cause macular or flat lesions which are benign or rarely malignant. These macular lesions are otherwise known as epidermodyplasia verruci formis (EV).

In a third group which infect particularly the genital tract there may be listed Types 6, 11, 34 and 39, 41-44, and 51-55 which cause condylomata which are rarely malignant, Types 13 and 32 which cause benign focal epithelial hyperplasia, Types 16 and 18 which cause epithelial dysplasia and other lesions considerable potential including bowenoid papulosis, and Types 30, 31, 33, 35, 45 and 56 which cause condylomata with intermediate malignant potential. The condylomata appear mostly in the anogenital tract and in particular the cervix. Types 16 and 18 are associated with the majority of in situ and invasive carcinomas of the cervix, vagina, vulva and anal canal. The condylomata may also occur in the aerodigestive tract.

In particular HPV16 is associated with premalignant and malignant diseases of the genito-urinary tract, and in particular with carcinoma of the cervix (Durst et al., PNAS 80 3812-3815, 1983; Gissmann et al., J. Invest. Dermatol 83 265-285, 1984). Presently, there is no information on the role of humoral responses in the neutralization of HPV16.

The detection of antibodies against HPV16 fusion proteins (Jenison et al., J Virol 65 1208-1218, 1990; Rachel et al, Int. J. Cancer 48 682-688, 1991) and synthetic HPV16L1 peptides (Dillner et al. Int. J. Cancer 45 529-535, 1990) in the serum of patients with HPV16 infection confirms that there are B epitopes within the capsid proteins of HPV, though few patients have HPV16 L1-specific antibodies identified by these techniques. There is no system for HPV16 propagation in vitro, and human genital lesions produce few HPV16 virions; therefore HPV16 particles have not been available for immunological studies.

The animal papilloma viruses may also include bovine papilloma virus (BPV) and in particular types BPV1, BPV2, BPV3, BPV4, BPV5 and BPV6 which are also differentiated by DNA sequence homology. In general the other animal papilloma viruses infect deer, horses, rabbits, dogs, rodents and birds. Papilloma viruses are small DNA viruses encoding for up to eight early and two late genes. (for review see Lancaster and Jenson 1987 Cancer Metast. Rev. p 6653-6664; and Pfister 1987 Adv. Cancer Res 48, 113-147). The organisation of the late genes is simpler than the early genes. The late genes L1 and L2 slightly overlap each other in most cases. The putative L2 proteins are highly conserved among different papilloma viruses particularly the sequence of 10 basic amino acids at the C-terminal end. The broad domain in the middle reveals only small clustered similarities. The L10RF however appears monotonously conserved in all known cases. (See Syrjanen et al above). The amino acid sequence homology reaches 50% with the comparison between HPV1a, HPV6b, BPV1 and CRPV (Cotton tail rabbit papilloma virus).

In regard to immunotherapy concerning papilloma virus infections prior methods of treatment of warts and epithelial skin lesions have involved the use of surgery which can be painful and traumatic with scarring often a result with the risk that reinfection can occur. Treatment with chemicals has also been used. A common treatment agent is salicylic acid which is the main ingredient in strengths ranging from 10% to 40% in tinctures and plasters. Formalin in strengths of 38-20% has also been proposed. Cryotherapy has been used for treatment of skin warts. Gluteraldehyde as a treatment agent has also been used. Podophyllin has also been used with varying success for both skin warts and anogenital condylomata. The types of surgery that has been used on anogenital condylomata has included surgical excision, cryosurgery and laser surgery. The use of interferons has also been proposed (see Syrjanen et al above).

Antibodies to the L1 protein of bovine papillomavirus (BPV) have virus-neutralization activity (Pilacinski et al., 1986) and HPV11 virions can be inactivated in an in vitro model by specific antisera (Christensen and Kreider, J. Virol 64 3151-3156, 1990). There is also some evidence that spontaneous regression of HPV1-induced cutaneous warts is associated with increased humoral immune responses to wart protein (Kirchner, Prog. Med. Virol 33 141, 1986).

Vaccines have also been proposed with indifferent success. It has been proposed to use vaccines containing autogenous tumor homogenates [Abcarian et al J. Surg Res 22: 231-236 (1977) Dis Colon Rectum 25:648-51 (1982) Dis Colon Rectum 19: 237-244 (1976)]. However it has recently been advocated that patients should no longer be treated with autogenous vaccines because of the potential oncogenic effect of the viral DNA (Bunney 1986 Br Med J 293 1045-1047).

In relation to production of genetically engineered vaccines this matter has been discussed in Pfister (1990) above and it seems that difficulty has been experienced in obtaining an effective vaccine because of the plethora of different papilloma virus types. Pfister however points out that attention should be directed to the so called early proteins (ie. E1, E2, E3, E4, E5, E6, E7 or E8) because these proteins are most likely synthesised in the proliferating basal cells of a wart infection in contrast to the structural proteins which are expressed in the upper epidermal layers. Therefore according to Pfister (1990) virus capsid protein appears to be limited in relation to use in a vaccine. The use of recombinant vaccinia viruses in in vitro test systems for papilloma virus early proteins in eukaryotic cells has been discussed also in Pfister (1990). This may take the form of a live vaccine consisting of genetically modified vaccina virus expressing papilloma virus proteins or on the surface of paraformaldehyde fixed autologous cells infected in vitro with vaccinia recombinants or transfected with other expression vectors. Another strategy for vaccine development as discussed in Pfister (1990) is to use an immune stimulating complex of the glycoside Quil A.

Data on successful proplylactic vaccination exist only for bovine fibropapillomas homogenised homogenate of bovine fibropapillomas and has been shown to provide limited immunity (Olson et al J Am Vet Med Assoc 135, 499 (1959) Cancer Res 22 463 (1962)). A vaccine including an engineered L1 fusion protein (Pilacinski et al. UCLA Symp. Molecular and Cellular Biology New Series Vol 32 papilloma Viruses Molecular and Clinical Aspects Alan R Liss New York 1985 257) has also been used in calves but proved unsuccessful in humans (Barthold et al J. Am. Vet Med. Assoc. 165, 276, 1974). In Pfister (1990) it is stated that there is presently no evidence for a possible prevention of HPV infection by the use of a capsid protein vaccine, but induction of an antitumor cell immunity appears to be feasible.

The L1 and L2 genes have been the basis of vaccines for the prevention and treatment of papilloma virus infections and immunogens used in the diagnosis and detection of papilloma viruses (International Patent Specifications WO8605816 and WO830623). However, it appears that no commercial usage of these vaccines have taken place.

SUMMARY OF THE INVENTION

Therefore it is an object of the invention to provide virus like particles (VLPs) which may be useful as diagnostic agents as well as forming a component of a vaccine for use with papilloma virus infections.

The invention therefore in one aspect includes a method for production of papilloma virus like particles (VLPs) including the steps of:

(i) constructing one or more recombinant DNA molecules which each encode papilloma virus L1 protein or a combination of papilloma virus L1 protein and papilloma virus L2 protein; and (ii) transfecting a suitable host cell with said one or more recombinant DNA molecules so that virus like particles (VLPs) are produced within the cell after expression of the L1 or combination of L1 and L2 proteins.

The invention in another aspect includes a vaccine containing the papilloma virus VLPs in combination with a suitable adjuvant.

In relation to step (i) only papilloma virus L1 protein is required to form VLPs of some papilloma viruses. Suitably only the L1 protein is required to form VLPs of BVP1, HPV11 and HPV6 including HPV6b. However VLPs may also be formed in relation to BPV1, HPV11 or HPV6b containing both L1 and L2 proteins. For the formation of VLPs of other papilloma viruses such as HPV16, both the L1 and L2 proteins are required. This situation is also believed applicable to HPV18 which has similar pathological symptoms to HPV16 and also similar DNA sequence homology. Further it will be appreciated that the L1 and L2 genes may be included in the same DNA recombinant molecule or in different DNA recombinant molecules.

Preferably the recombinant DNA molecules are contained in recombinant virus which may transfect the host cell. Suitable viruses that may be used for this purpose include baculovirus, vaccinia, sindbis virus, SV40, Sendai virus, adenovirus, retrovirus or poxviruses. Suitable host cells may include host cells that are compatible with the above viruses and these include insect cells such as *Spodoptera frugiperda*, CHO cells, chicken embryo fibroblasts, BHK cells, human SW13 cells, drosophila, mosquito cells derived from *Aedes albopictus* or monkey epithelial cells. It will also be appreciated that other eukaryote cells may comprise yeast cells or other mammalian cells.

The DNA recombinant molecule is suitable obtained from a source of papilloma virus genome whereby L1 protein or L2 protein may be amplified by PCR amplification using suitably designed primers discussed hereinafter. Preferably a gene encoding L1 protein is inserted in a plasmid containing a suitable promoter and a DNA fragment containing the L1 protein and promoter is incorporated in a primary plasmid which may constitute the recombinant DNA molecule which may be inserted into a recombinant virus vector as described above.

A gene encoding the L2 protein may also be linked to a suitable promoter and preferably a DNA fragment incorporating the L2 gene and promoter is inserted into the primary plasmid to provide a doubly recombinant plasmid or secondary plasmid which plasmid may also be inserted in a recombinant virus vector as described above to form a doubly recombinant virus vector.

However the invention also includes the embodiment wherein the primary plasmid and/or the secondary plasmid may infect a suitable host cell to produce VLPs containing L1 protein or VLPs containing L1 and L2 protein under appropriate experimental conditions. The latter VLPs are the ideal immunogen for a papilloma virus specific vaccine, as the L2 protein is immunodominant in natural infection.

Other suitable DNA recombinant molecules include cosmids as well as recombinant viruses. Suitable expression systems include prokaryotic expression systems including *E coli* and any plasmid or cosmid expression vector or eukaryotic systems including host cells described above in combination with a recombinant virus vector or alternatively yeast cells and yeast plasmids.

In the situation where plasmids are used which incorporate genes encoding L1 or both L1 and L2 and wherein such plasmids may infect a suitable host cell for production of VLPs such plasmids should also include a suitable promoter to enhance expression of the VLP structural proteins and a polymerase may also be utilised which is associated with the relevant promoter. However in this situation VLPs may only be obtained under specific experimental conditions.

The L1 and L2 genes may be driven off any mammalian or viral promoter with a mammalian or viral polyadenylation signal. Preferably the L1 and L2 genes are transcribed from any vaccinia virus promoter which may be an early promoter or late promoter as considered appropriate. A list of such promoters is given in Davision and Moss (1989) J. Mol. Biol. 210 749-769 and (1989) J. Mol. Biol. 210 771-784.

In the experimental work that has taken place the L1 gene is located downstream of a vaccinia 4b promoter and the L2 gene is located downstream of a synthetic vaccinia 28 k late promoter. The host cell is monkey epithelial cells.

The VLPs may be obtained from the transfected cells by any suitable means of purification. The VLPs may be combined with any suitable adjuvant such as ISCOMS, alum, Freunds Incomplete or Complete Adjuvant, Quil A and other saponins or any other adjuvant as described for example in Vanselow (1987) S. Vet. Bull. 57 881-896.

Reference may now be made to various preferred embodiments of the invention as illustrated in the attached drawings. In these preferred embodiments it should be noted that the specific papilloma viruses, VLPs and specific constructs of DNA recombinant molecules are given by way of example.

BRIEF DESCRIPTION OF THE DRAWINGS

FIGS. 2A and 2B are a western blot analysis of recombinant HPV16 L1 in vaccinia virus infected CV-1 cells.

FIGS. 9 and 10 illustrate mapping results for sera from BLAB/c, C57B1/6, and CBA mice immunized with synthetic HPV 16 capsids and pooled CFA immunised control sera.

EXAMPLE 1

VLPS Derived from HPV16

The HPV-16 L1 gene, from the second ATG (nt5637), was amplified by polymerase chain reaction from pHPV16 (provided by Dr. L. Gissmann), using following primers:

```
                                           (SEQ ID NO: 54)
1/ 5'-CAGATCTATGTCTCTTTGGCTGCCTAGTGAGGCC-3'

(SEQ ID NO: 55)
2/ 5'-CAGATCTTTACAGCTTACGTTTTTTGCGTTTAGC-3'
```

The first methionine codon and stop codon are indicated by underline, and BqlII sites were included to facilitate subcloning. The amplified 1527 bp fragment was extracted with phenol and purified by 1% agarose gel electrophoresis. After digestion with BglII the L1 gene was subcloned into the BamHI site of the RK19 plasmid (Kent 1988 Ph.D. thesis, University of Cambridge) which contains a strong vaccinia virus promoter (4b). The resulting plasmid was sequenced (Sanger et al, 1977, Proc. Natl. Acad. Sci. USA 74, 5463-5467) and used to prepare a fragment containing the HPV16 L1 gene linked to the 4b promoter by digestion with MluI and SstI. This fragment was blunted with T4 DNA polymerase and cloned into the Bam HI site of the vaccinia intermediate vector pLC1, which contains the B24R gene of vaccinia virus (Kotwal and Moss, 1989, J. Virol. 63, 600-606; Smith et al, 1989, J. Gen. Virol. 70, 2333-2343), an E. coli gpt gene (Falkner and Moss, 1988, J. Virol. 64, 1849-1854; Boyle and Coupar, 1988, Gene 65, 123-128) and multiple cloning sites to produce plasmid pLC200.

The HPV16 L2 gene was prepared by partial digestion of pHPV16 with AccI to produce a fragment (4138 nt-5668 nt) which was filled with Rlenow and linked to synthetic BamHl linkers. This L2 fragment was cloned into the Bam HI site of a pUC derived plasmid termed p480 which has a synthetic vaccinia 28R late promoter, with some modifications (Davison and Moss, 1989, J. Mol. Biol. 210, 771-784). The promoter sequence is as follows:

```
                                           (SEQ ID NO: 56)
5'-GAGCTCTTTTTTTTTTTTTTTTTTTGGCATATAAATGGAGGTACC
C-3'
``` the late promoter motif is underlined. A fragment containing the L2 gene linked to the 28R promoter was isolated by digestion with SstI/SalI, blunted by T4 DNA polymerase and then cloned into the SstI and SalI sites of pLC200 to produce pLC201 (FIG. 1).

Figure 1:
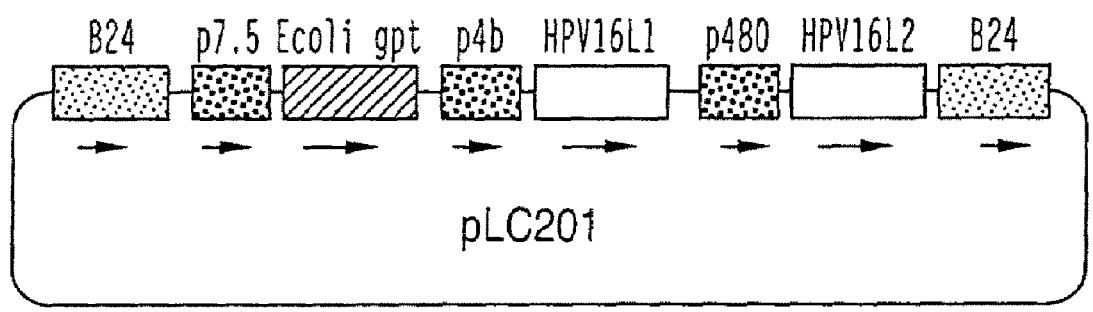
FIG. 1 is a schematic representation of plasmids used to construct HPV16 recombinant vaccinia viruses.

In FIG. 1, HPV16 L1, L2 (open boxes) are under control of vaccinia late promoters (solid boxes). E. coli gpt gene (shaded box) is used as selection marker. Flanking sequence for homologous recombination. The direction of transcription is indicated by arrows.

The pLC201 plasmid was then used to construct a recombinant vaccinia virus as previously described (Mackett et al, 1984, J. Virol. 49, 857-864). Recombinant virus pLC201W and pLC202VV were selected by plaque assay in the presence of mycophenolic acid, xanthine, and hypoxanthine (Falkner and Moss, 1988). Recombinant vaccinia virus (VV) expressing HPV16L1, and HPV16L2, were prepared and used as previously described (Zhou et al, 1990, J. Gen. Virol. 71, 2185-2190).

Recombinant plasmid pLC201 was deposited with the American Type Culture Collection, 12301 Parklawn Drive, Rockville, Md. 20852, U.S.A. on 27 Mar., 1992 and given the designation 75226.

Recombinant vaccinia virus pLC201VV was deposited with the American Type Culture Collection, 12301 Parklawn Drive, Rockville, Md. 20852, U.S.A. on 3 Apr., 1992 and assigned the designation VR2371.

Purification of Virus-Like Particles

CV-1 cells infected with recombinant viruses pLC201VV were harvested in 10 mM Tris (pH 9.0) 32 hr after infection and homogenised with a Dounce homogeniser. Homogenates were clarified by centrifugation at 2000 g to remove the cell debris and layered onto a 30% (wt/vol) sucrose cushion. The pellet formed by centrifugation at 110,000 g in a SW38 rotor for 90 min was suspended in 10 mM Tris pH9.0 and layered onto a 20-60% discontinuous sucrose gradient. After centrifugation at 100,000 g for 18 hrs, 10 equal fractions of 0.25 ml were collected. Samples were mixed with 0.6 ml ethanol. The pellet obtained after centrifugation at 40 C and 12000 g for 20 minutes was collected for further analysis. To determine the density of the virus-like particles, equilibrium density-gradient sedimentation was accomplished in CsCl (1.30 g/ml). After centrifugation at 125,000×g for 20 hrs, 11 fractions of 0.25 ml were collected. The density of each fraction was determined, and each was examined for virus-like particles by transmission electron microscopy.

Figure 2A:
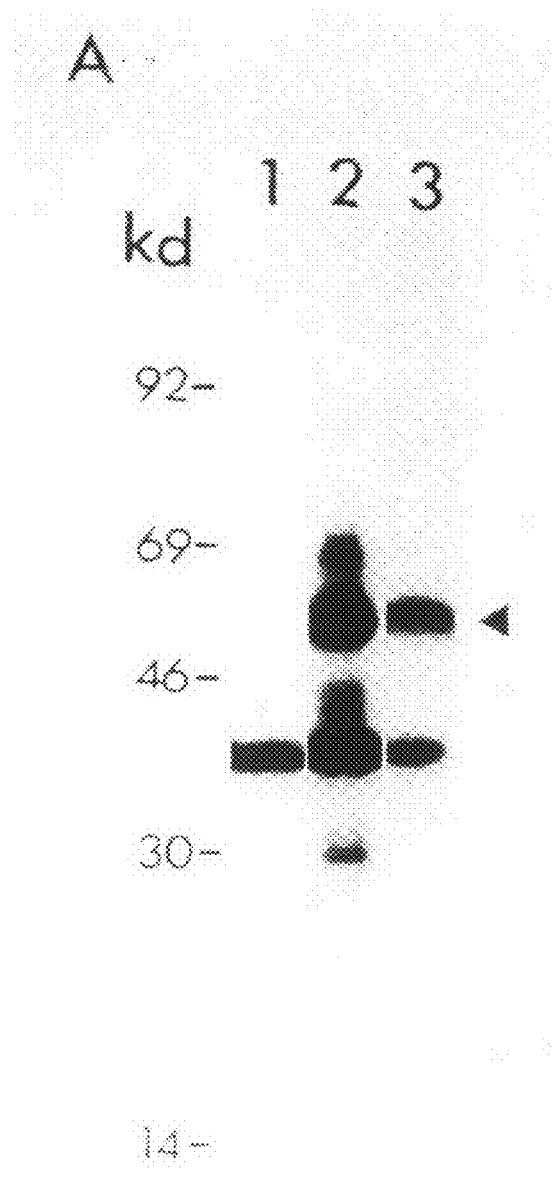
Figure 2B:
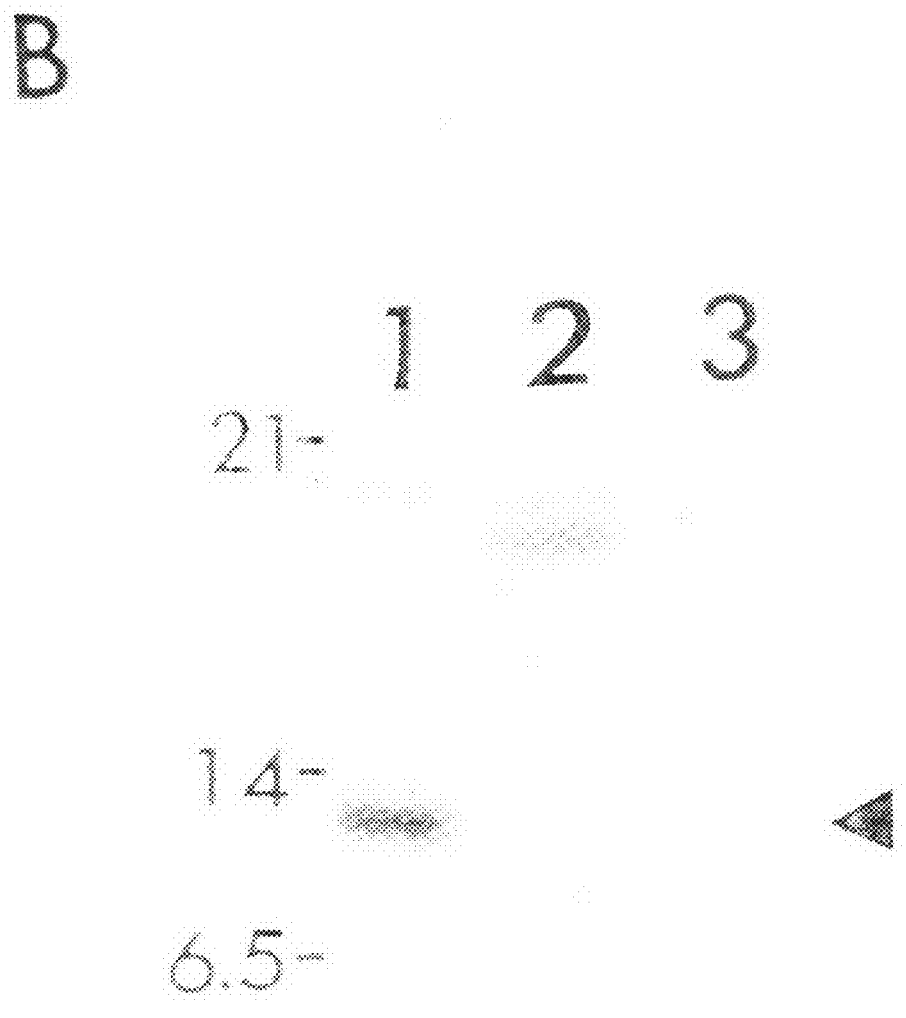

In FIG. 2A cells were infected at 10 pfu/cell with wt VV (lane 1) and pLC201VV (lane 2) and harvested 48 h post infection. L1 proteins was detected with the HPV16 L1 specific MAb Camvir 1. The 57 kDa L1 protein is indicated by the arrow. Binding of Camvirl to the 35 kDa protein in all three lanes is non-specific.

Figure 3:
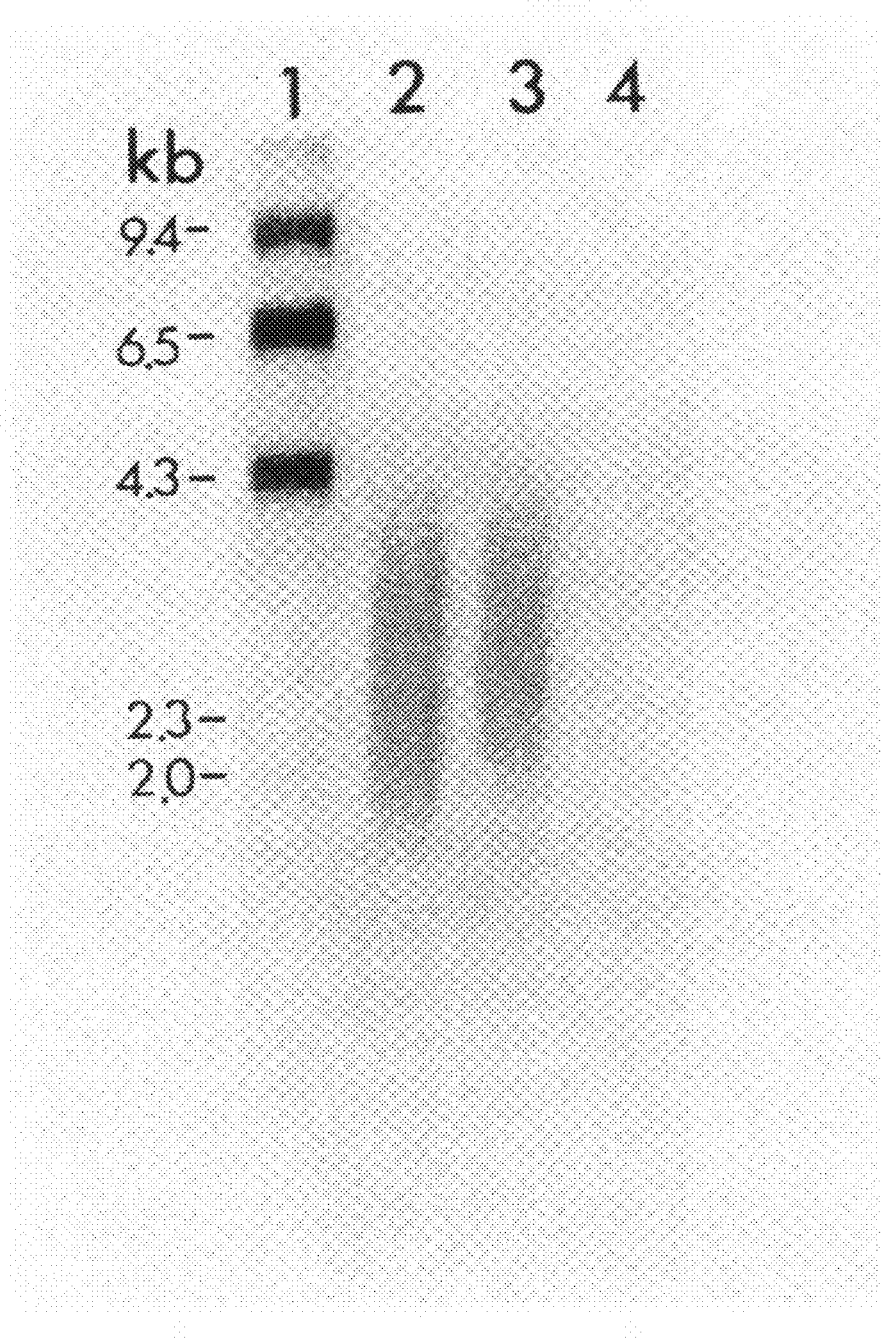
FIG. 3 is a northern blot analysis of recombinant vaccinia virus infected CV-1 cells.

In FIG. 3 RNAs extracted from cells infected with pLC201VV (lane 2), pLC202VV (lane 3) which also incorporates genes encoding HPV16 proteins E1 and E4 as well as genes encoding HPV16 L1 and L2 or wt VV (lane 4) were resolved on a 1.2% formaldehyde-agarose gel. RNA was transferred to nylon membrane and hybridised with a $^{32}$P-labelled L2 probe. Formaldehyde-treated lambda DNA Hind III cut marker are shown (lane 1).

Electron Microscopy

CV-1 cells infected with recombinant vaccinia virus were fixed in 3% (vol/vol) glutaraldehyde in 0.1M sodium cacodylate buffer and postfixed in 1% osmium tetroxide, dehydrated in graded alcohols, and embedded in epoxy resin. Thin section were cut and stained with uranyl acetate and lead citrate. Fractions from the sucrose gradient were dried onto EM grids, and negatively stained with 1% (wt/vol) phosphotungstic acid (pH7.0). Fractions were examined using a JEOL 1200Ex Transmission electron microscope.

Figure 4A:
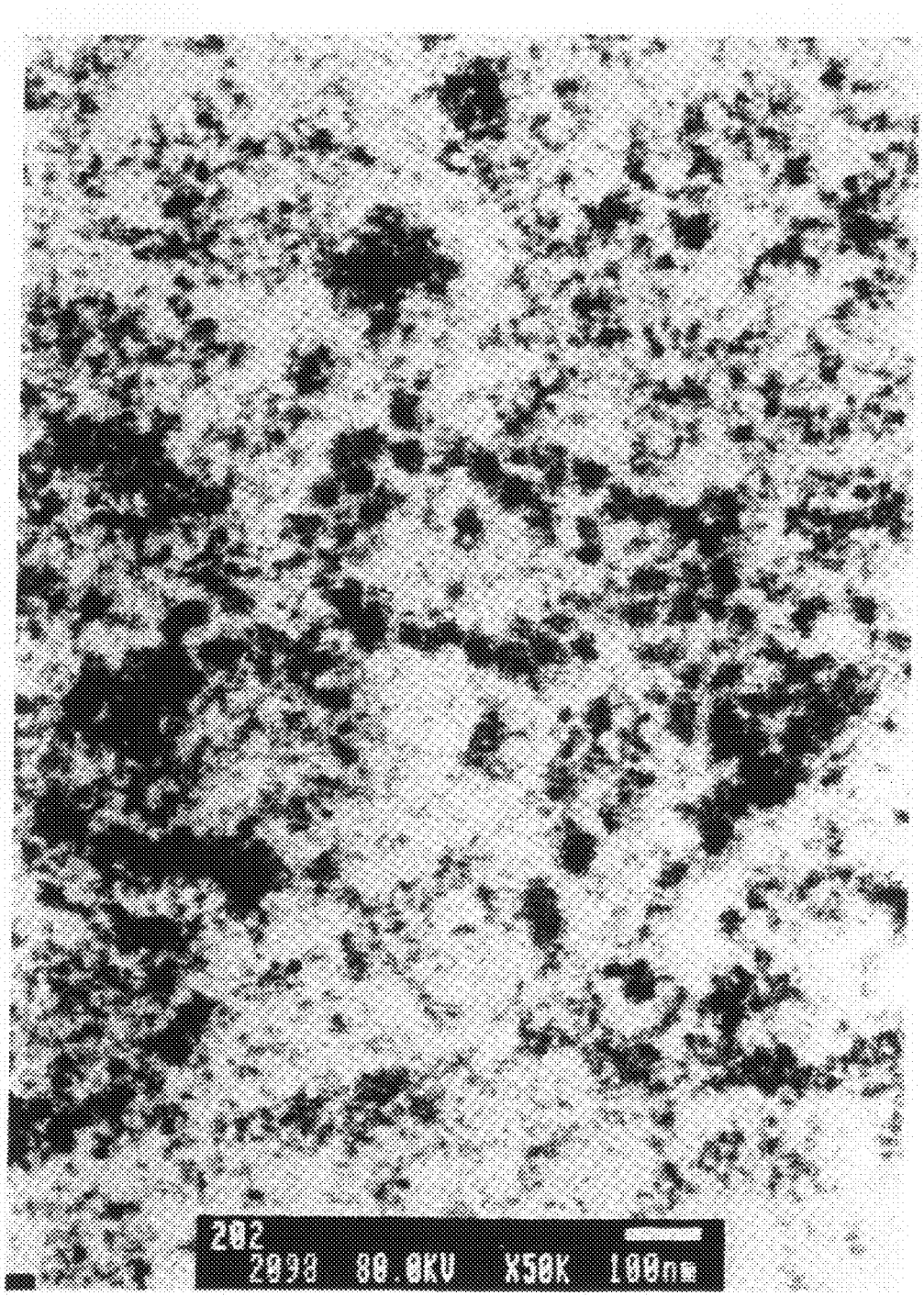
FIGS. 4A and 4B are electron microscopy of HPV virus-like particles from CV-1 cells infected with recombinant vaccinia virus.

In FIG. 4A there is shown CV-1 cells infected with pLC201W for 32 hours. In the CV-1 nuclei, particles of approximately 40-nm diameter (arrowed) were frequently found. The bar corresponds to 100 nm.

Figure 4B:
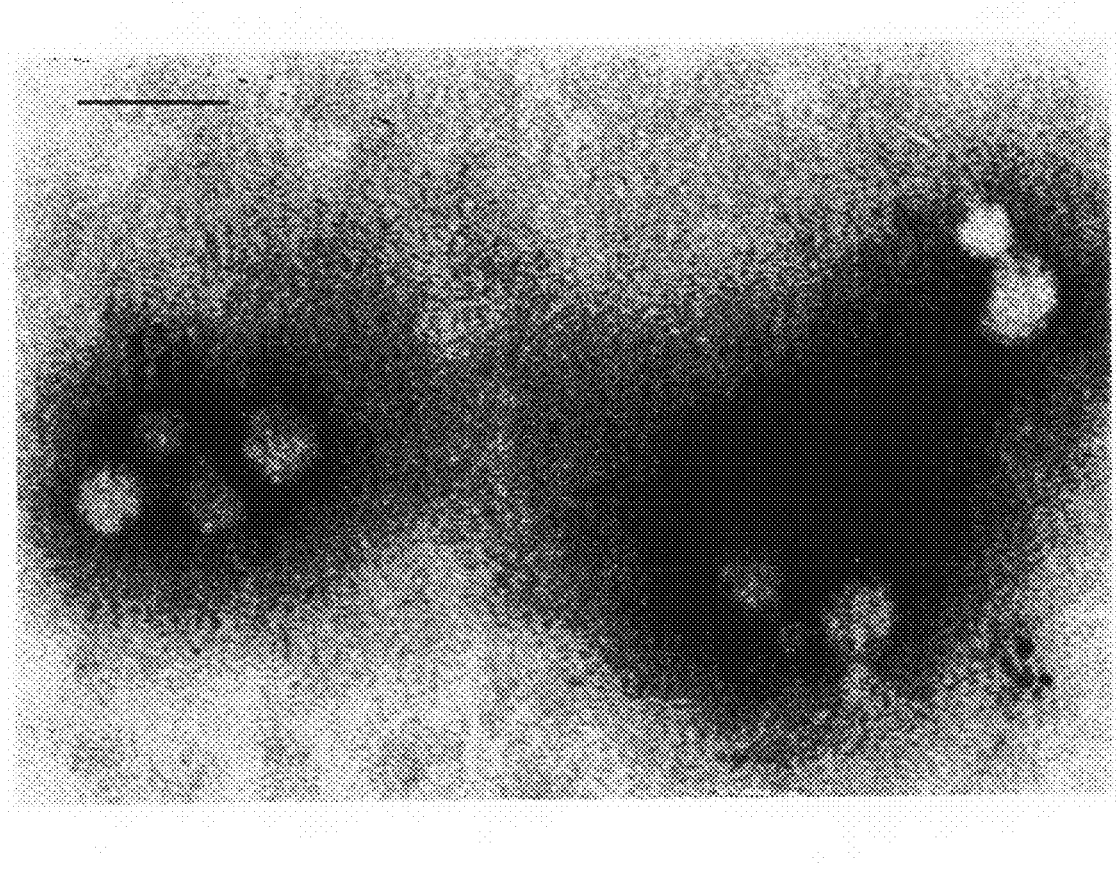

In FIG. 4B there is shown fraction 5 of the sucrose gradient. Papilloma virus-like particles, apparently consisting of regular arrays of capsomeres were observed (arrowed). The bar corresponds to 50 nm.

Analysis of HPV ORF Products

HPV16 L1 expression was analysed by immunoprecipitation and immunoblot. For immunoprecipitation, $^{35}$S metabolically labelled recombinant VV infected CV-1 cells were lysed in RIPA buffer 0.1% SDS. 1% Triton X-100, 1% sodium deoxycholate, 150 mM NaCl, 0.5 g/ml aprotinin, 10 mM Tris-HCl, pH7.4). Immunoblot analysis of partially purified virus-like particles, using the L1 specific MAb Camvirl (Mclean et al, 1990, J. Clin. Pathol. 43, 488-492) and $^{125}$I antimouse IgG (Amersham), was performed as previously described using samples solubilised in 2×SDS gel loading buffer containing 2-mercaptoethanol. Analysis of HPV16 L2 gene expression is shown in FIG. 13B. For analysis of N-glycosylation, partially purified virus-like particles were taken up to 100 l buffer (0.25 M sodium acetate, pH6.5, 20 mM EDTA and 10 mM 2-mercaptoethanol) and reacted with 0.5 u Endoglycosidase F (Boehringer Mannheim) at 370 C for 18 hrs prior to immunoblotting.

Mycophenolic acid was used to select a vaccinia virus recombinant for the gnt plasmid pLC201 and this was termed pLC201VV. Synthesis of L1 in cells infected with pLC201VV was confirmed by immunoblotting and immunoprecipitation. L1 protein was demonstrated as a band on autoradiography of approximately 57 kDa. A northern blot of RNA extracted from CV-1 cells infected with these recombinant viruses confirmed high levels of L2 mRNA transcription in cells infected with either of these viruses (FIG. 3). L2 transcription from a synthetic vaccinia virus late promoter gave a heterogeneous Northern blot pattern because VV late—RNAs do not use a specific transcription termination signal.

CV-1 cells were infected with pLC2O1VV and examined for virus-like particles. Electron micrographs of thin sections of cells infected with pLC201VV, but not of control cells infected only with wild-type vaccinia, showed approximately 40 nm virus-like particles in cell nuclei. In most cases these particles were linked in chains, and near the nuclear membrane (FIG. 4a). Cells infected with recombinant vaccinia viruses which expressed HPV16 L1 only or L2 only, and produced the corresponding protein (L1) or mRNA (L2), did not contain virus-like particles. Cells simultaneously infected with two different recombinant vaccinia viruses, which expressed HPV16 L1 and HPV16 L2 respectively, also failed to make any HPV virus-like particles; although L1 protein and L2 mRNA could be identified in pools of these double infected cells simultaneous synthesis of both L1 and L2 within individual cells was not demonstrated.

Figure 5:
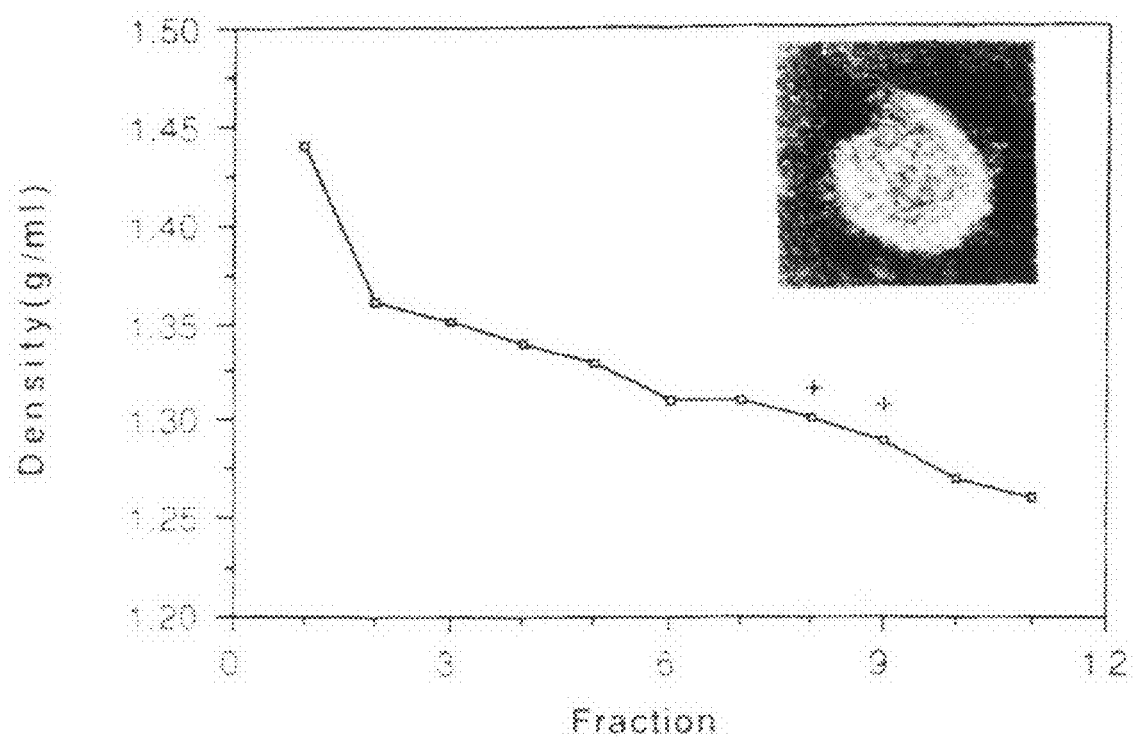
FIG. 5 illustrates CsCl equilibrium density gradient sedimentation of HPV16 empty capsids.

In FIG. 5 HPV16 virus-like particles obtained from CV-1 cells infected with pLC201VV were centrifuged over a sucrose cushion and then subjected to CsCl isopynic sedimentation. Virus-like particles (+) were found in fractions 8 and 9. The transmission electron micrograph of a negatively stained particle from fraction 8 is shown in the insert. The density (g/ml) of each gradient fraction is indicated.

Figure 6:
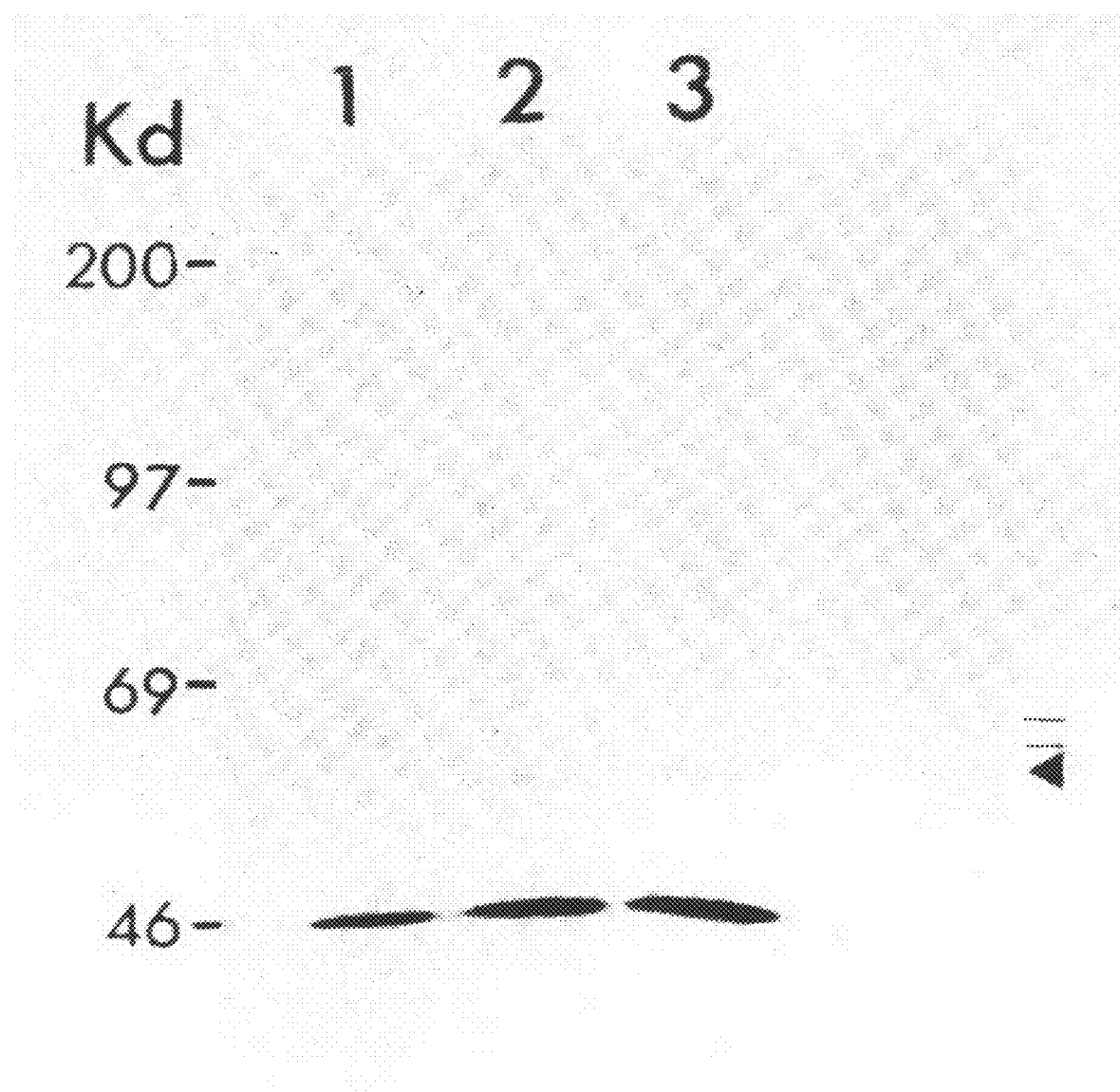
FIG. 6 illustrates Glycosylation of L1 proteins in purified virus particles.
Figure 7:
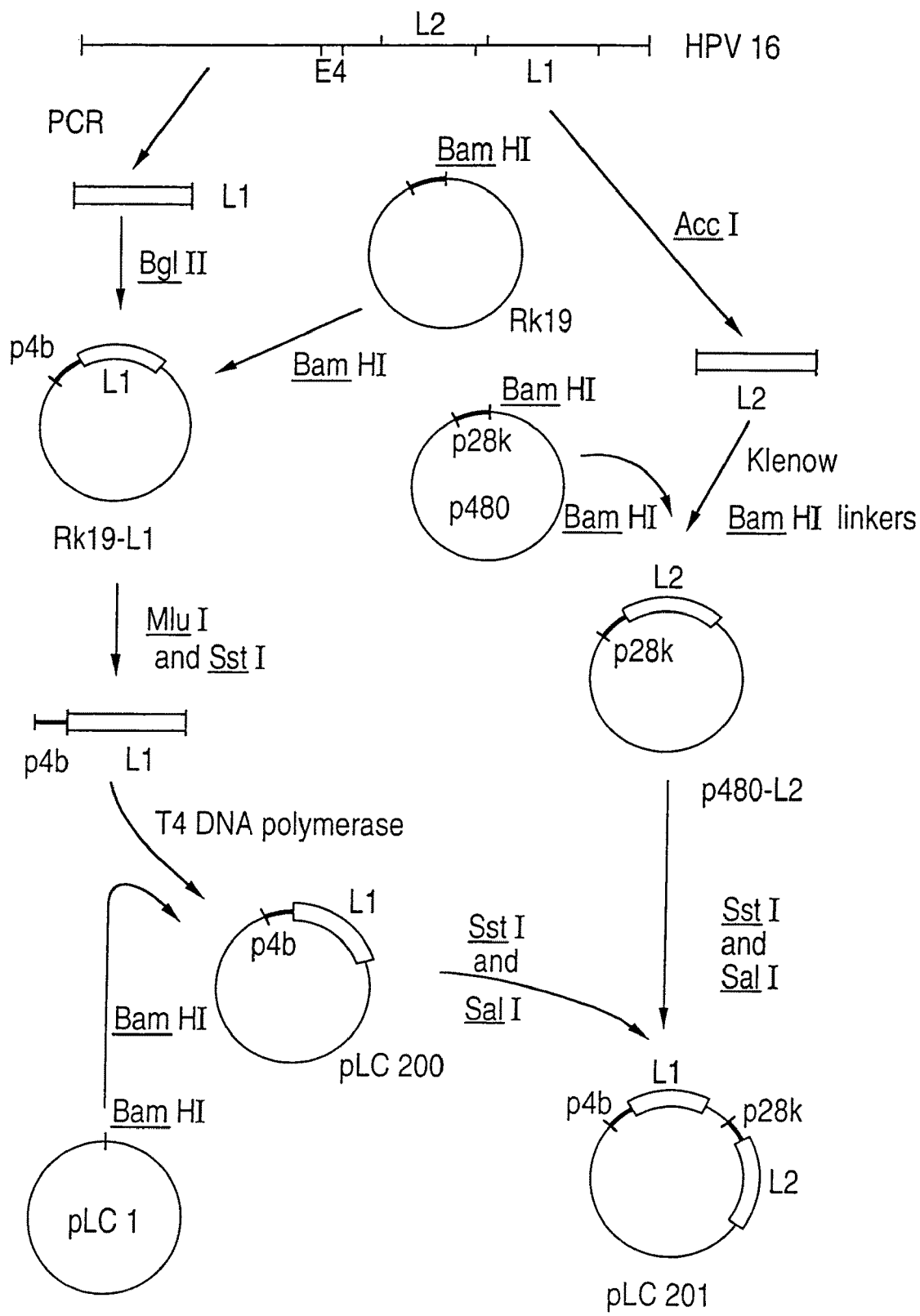
FIG. 7 is a flow diagram of the constructions of plasmid pLC200 encoding L1 and pLC201 encoding L1 and L2.

In FIG. 6 CV-1 cells were infected with pLC201VV for 32 hrs, and virus-like particles were purified on a sucrose gradient. Samples were precipitated with ethanol and treated with endoglycosidase F before analysis by immunoblotting with an anti-HPV16 L1 antibody Camvir I. Lane 1: purified virus-like particles; Lane 2 and 3: after treatment with endoglycosidase F overnight. The L1 doublet is indicated by (=), and deglycosylated L1 is indicated by the arrow. Molecular weight markers are shown on the left.

To confirm that the virus-like particles observed by electron microscopy contained HPV16 L1 protein, cell extracts from pLC2O1VV infected cells were subjected to a partial purification in a 20%-60% sucrose gradient. Ten fractions were collected and examined for L1 protein. From fractions 3 to 7, L1 could be detected and in fraction 5, the highest level of L1 was found. Each fraction was also examined by EM for virus-like particles: these were observed in fraction 5. A typical papilloma virus negatively-stained with sodium phosphotungstate, has 72 regular close-packed capsomeres (Finch and Klug, 1965, J. Mol. Biol. 13, 1-12; Rowson and Mahy, 1967, Bacteriol. Rev. 31, 110-131) and has a diameter about 50 nm. The diameter of the virus-like particles purified from the infected CV-1 cells varied between 35 nm and 40 nm. These virus-like particles however possessed a similar EM appearance to papilloma viruses, and a regular array of capsomeres could be recognised (FIG. 4b). The virus-like particles identified in fraction 5 of the sucrose gradient were therefore presumed to be empty and incorrectly assembled arrays of HPV capsomeres. In CsCl, HPV16 virus-like particles sedimented at about 1.31 g/ml (FIG. 5), and showed a typical empty papilloma virus capsid appearance under transmission electromicroscope (FIG. 5, insert).

Canvir-1 identified a protein doublet in western blots of virus-like particles purified from pLC20iVV infected CV-1 cells (FIG. 6). HPV16 L1 contains four potential N-glycosylation sites (asparagine 157, 242, 367 and 421). To test whether the doublet represented glycosylation variants of the L1 polypeptide, partially purified virus-like particles were subjected to treatment with endoglycosidase F, prior to SDS-PAGE and immunoblotting. This resulted in the replacement of the doublet by a single band of slightly lower apparent molecular weight, at the expected molecular weight of about 57 kDa (FIG. 6. lane 2, 3).

The virus-like particles collected from fractions of the CsCl gradient with a buoyant density of 1.29-1.30 g/ml were used as antigen in an ELISA assay. All antisera from mice immunised with VLPs were positive (Table 2). Control sera from mice immunized with the similar fractions of a density gradient prepared with lysate of CV-1 cells infected with wild type vaccinia were nonreactive with the virus-like particles. Using two different protocols to coat virus-like particles to ELISA plates (Dillner et al., 1991, J Virol 65, 68626871), attempts were made to distinguish reactivity with native HPV virus-like particles from reactivity with the partially denatured proteins of disrupted particles. The murine antisera raised against the VLPs were equally reactive with the native (OD 1.00+0.20) and denatured (OD 1.60+0.45) particles. A panel of 6 monoclonal antibodies specific for defined L1 epitopes included only 1 (Camvir 1) that was weakly reactive (OD 0.064) with native VLPs, and it proved more reactive with denatured particles (OD 0.107) than with native particles, suggesting that the reactivity was with denatured L1 protein in the native VLP preparation.

Figure 8:
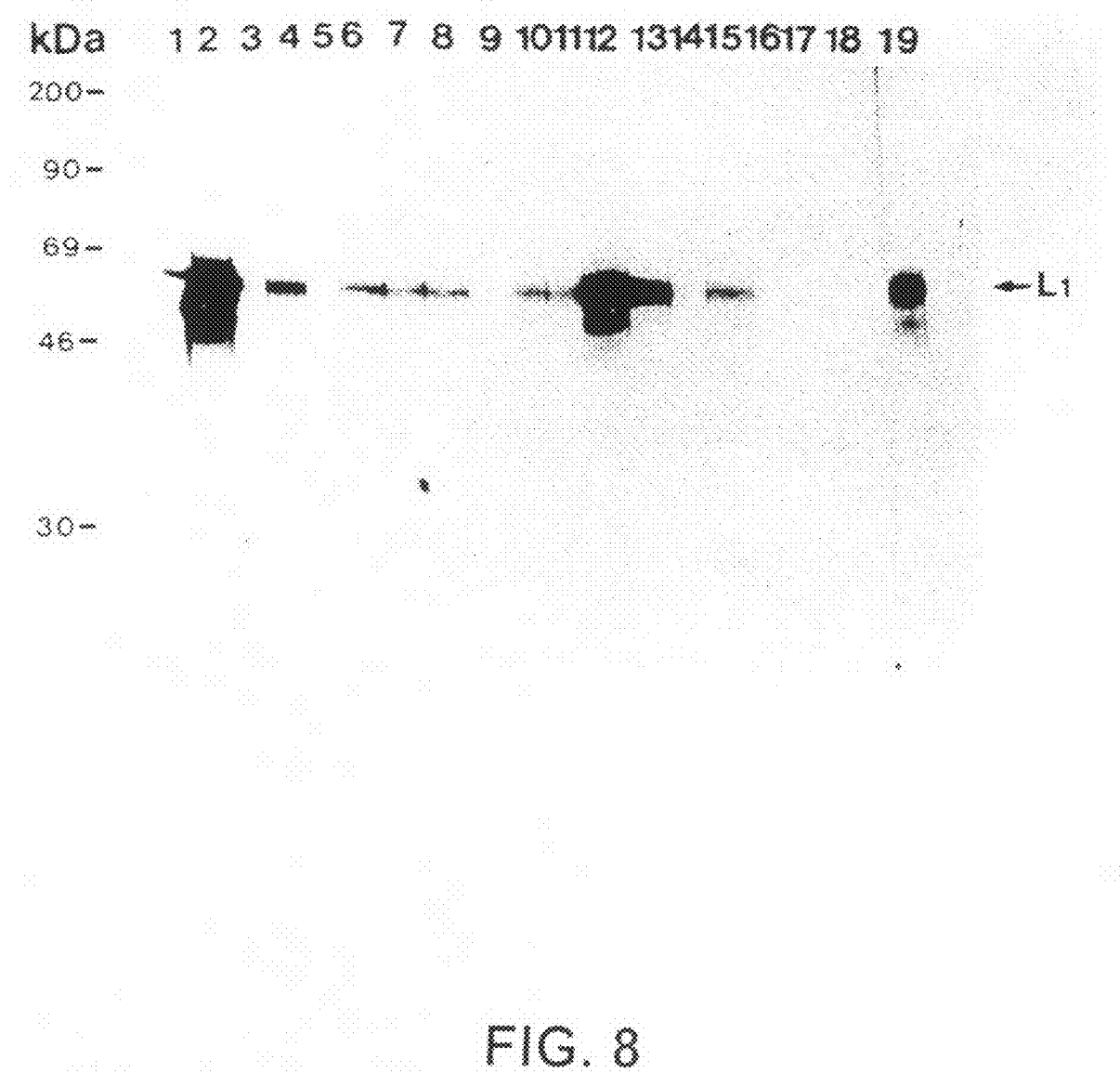
FIG. 8 is a western blot analysis of the reactivity of murine sera with baculovirus recombinant L1 protein.

In FIG. 8 $^{125}$I-labelled anti-mouse IgG was used as the second antibody. The 57-kDa L1 band is indicated by the arrow. Key: sera from individual mice immunized with VLPs: lanes 1-5, BALB/c; lanes 6-10, C57B1/6; lanes 11-15, B1OA; sera from individual mice immunized with CFA; lane 16, BALB/c; lane 17, C57B1/6; lane 18, B1OA; anti-HPV 16L1 MAb Camvir 1, lane 19. The molecular weights are indicated on the left.

Reactivity of the anti-VLP antisera with the L1 and L2 proteins of HPV16 was confirmed by immunoblot using baculovirus recombinant HPV16 L1 and L2 proteins. Sera from all mice immunized with the virus-like particles, and each of the monoclonal anti-HPV 16 L1 antibodies, recognized a 57-kDa protein (FIG. 8) in the L1 recombinant-baculovirus-infected *S. frugiperda* cell lysates, and no comparable reactivity was observed with lysates of *S. frugiperda* cells infected with wild-type baculovirus. The intensity of reactivity with the L1 protein varied from mouse to mouse, but all sera were reactive with prolonged exposure of the immunoblots. Similar results were obtained with the L2 recombinant baculovirus-infected cell lysates: murine anti-VLP antisera and a rabbit antiserum to L2 protein both reacted with a single protein in the lysate. Sera from mice immunized with CFA alone failed to react with protein from lysates of L1 or L2 recombinant baculovirus-infected *S. frugiperda*.

EXAMPLE 2

Definition of Linear Antigenic Regions of HPV16L1 Protein Using VLPS

In a further series of experiments the linear antigenic regions of the HPV16 L1 capsid protein using synthetic VLPs were determined. In such experiments mice of three haplotypes (H-$2^d$, H-$2^b$, and H-$2^{d/b}$) were immunized with synthetic HPV16 virus-like particles (VLPs), produced using a vaccinia virus doubly recombinant for the L1 and L2 proteins of HPV16. The resultant-anti-VLP antisera recognized HPV16 capsids by ELISA assay and baculovirus recombinant HPV16L1 and L2 protein on immunoblot. Overlapping peptides corresponding to the HPV16L1 amino acid sequence were used to define the immunoreactive regions of the L1 protein. The majority of the L1 peptides were reactive with IgG from the mice immunized with the synthetic HPV16 capsids. A computer algorithm predicted seven B epitopes in HPV16 L1, five of which lay within peptides strongly reactive with the murine antisera. The murine anti-VLP antisera failed to react with the two peptides recognized by anti-HPV16L1 monoclonal antibodies raised by others against recombinant L1 fusion protein. We conclude that the immunoreactive epitopes of HPV16 defined using virus-like particles differ significantly from those defined using recombinant HPV16L1 fusion proteins, which implies that such fusion proteins may not be the antigens to look for HPV16L1 specific immune responses in HPV-infected patients.

Production of HPV16 capsids. Plasmid pLC201 containing HPV16L1 and L2 open reading frames (ORFs) under the control of vaccinia virus promoters 4b (natural) and p480 (synthetic) was used to construct the recombinant vaccinia virus (rVV) pLC2O1VV as previously described but with exceptions as mentioned below. HPV16 virus-like particles were prepared from pLC201VV infected CV-1 cells as mentioned previously, but cells were cultured in medium containing rifampicin at 100 g/ml to prevent the assembly and maturation of vaccinia virus (Moss, "Virology" p685-703 Raven, New York, 1985; Raracostas et al., PNAS 86, 8964-8967, 1989). The infected cells were harvested and lysed by freezing and thawing following Dounce homogenization in 10 mM Tris-HCl (pH 9.0). Lysates were clarified by centrifugation at 2000 g and then spun at 100,000 g for 2 hr over a 20% sucrose cushion in PBS buffer. The pellet was mixed with CsCl to an initial density of 1.30 g/ml and centrifuged at 100,000 g for 18 hr at 18°. Fractions were collected and immunoblots were performed on ethanol-precipitated proteins. Fractions testing positive for L1 protein were pooled, and the presence of virus-like particles confirmed by electron microscopy as described above.

Production of antisera. Groups of five mice BALB/c (H-$2^d$), C57B1/6 (H-$2^b$), and B1OA (H-$2^{b/d}$) were immunized with CsCl gradient-purified HPV16 virus-like particles. Animals were inoculated with 5 g of capsid protein by subcutaneous injection. The initial injection was given with Freund's complete adjuvant, and three further injections at 3 weeks' intervals were given in saline. Fourteen days after the fourth injection, sera were collected and stored at −20°. Material prepared from CV-1 cells infected with wild type vaccinia virus, and processed exactly as for pLC201VV infected cells, was used to immunize control groups of mice according to the same protocol.

Peptides. A series of 15-mer peptides, overlapping by five residues, and spanning the deduced amino acid sequence of HPV16L1 protein (Seedorf et al., 1985, Virology 145 181-185; Parton, 1990, Nucleic Acids Res 18 363) was synthesized with the DuPont RaMPS multiple peptide synthesis system using Fmoc chemistry according to standard protocols (Fields and Noble, 1990 Int. J. Pept. Protein Res 35 161-214) and then conjugated with glutaraldehyde to bovine serum albumin (BSA). To denote the position of the amino acids (aas) in the L1 protein, the putative first initiation codon was designated amino acid number 1 (Table 1). For technical reasons the C-terminal peptide corresponding to aas 521531 was not used. All peptides used were of greater than 85% purity as judged by HPLC analysis.

Recombinant L1+L2 proteins. Recombinant baculoviruses expressing the HPV16L1 or the HPV16L2 ORF were used to infect insect SF9 cells. After 3 days incubation at 25°, cells were pelleted by centrifugation at 14,000 g for 5 min. The pellet was dissolved in RIPA buffer (20 mM Tris-HCl, pH 7.6; 2 mM EDTA; 50 mM NaCl; 1% deoxycholate; 1% Triton X-100; 0.25% SDS; 1% aproptinin; 1 mM PMSF).

Western blotting. Virus like particles or recombinant L1 or L2 protein were mixed with 2× loading buffer containing 2% SDS/DTT and boiled for 5 min. The proteins were separated in 10% polyacrylamide gels and blotted onto nitrocellulose (Towbin et al., 1979, Virology 175 1-9). Filters were cut into strips, incubated in 3% BSA in PBS at 37° for 1 hr. Blocked strips were exposed to the various murine antisera (1:200) or monoclonal antibodies overnight at 40. The reactive proteins were visualized by autoradiography after reaction with $^{125}$I-conjugated anti-mouse IgG (0.2 Ci/ml) (Amersham).

ELISA assay. Polyclonal antisera were tested for reactivity with synthetic HPV16 capsids by an enzyme linked immunosorbent assay (ELISA) as previously described (Christensen et al., 1990, PNAS 76 4350-4354, Cowsert et al., 1987, JNC1 79 1053-1057). For assays with "native" synthetic HPV16 capsids, 100 ng of protein in PBS (pH 7.5) was attached to each ELISA plate well (Flow Labs) by incubation for 1 hr at 37°. For assays with "denatured" particles, the particles were suspended in carbonate buffer, pH 9.6, and adsorbed on to the plate overnight at 37°. All subsequent incubations were done at room temperature. The plates were washed with PBS, and unattached sites were blocked by incubation for 1 hr in blocking buffer (5% milk powder in PBS, pH 7.5). The murine antisera (1:200), previously absorbed with wildtype VV-infected CV-1 cell extract, were added and incubated for 1 hr, and the plates were washed with PBS. Horseradish peroxidase-conjugated anti-mouse IgG (Sigma) at 1:1000 dilution in blocking buffer was added and incubated for 1 hr, followed by 10 washes with PBS. Substrate buffer (pH 4.6) containing ABTS (Boehringer) and $H_2O_2$ was added and the OD415 read after 15 min.

Linear B epitope mapping. B epitopes were identified by screening antisera from immunized animals against the set of overlapping HPV16L1 peptides by ELISA. Synthetic peptides coupled to BSA were diluted in 10 mM sodium carbonate buffer (pH 9.3) and adsorbed to ELISA plates overnight at 4°. Blocking of residual binding sites on the plates was carried out using 3% BSA in PBS for 2 hr at 37° Diluted mouse antisera (1:500) were incubated with coated plates at room temperature for 2 hr. The plates were washed with PBS containing Tween 20 (0.1%) and incubated with peroxidase-conjugated antimouse IgG (1:1000) (Sigma) or IgA (1:2000) (Sigma) for 2 hr. Plates were washed and developed with 0.5 mg/ml ABTS in substrate buffer (pH 4.6) for 15 min before recording absorbance values at 415 nm. A peptide was considered reactive if the OD 415 value with the test serum was greater than 3 SDs above the mean for the control serum: this gave a cut-off value of 0.260. An OD 415 of five times the mean OD 415 obtained with control sera (0.55) was arbitrarily considered to define a major reactive epitope.

Monoclonal antibodies and antisera. Five monoclonal antibodies (MAb) raised against HPV16L1 fusion protein were used. MAb 5A4, ID6, 3D1, and 8C4 (Cason et al., 1989, J. Gen Virol 70 2973-2987) were provided by Dr. Phil Shepherd from London, U.R. and MAb Camvir 1 (McLean et al., 1990, J. Clin. Pathol. 43 488-492) was obtained from Dr. C. McLean (Department of Pathology, University of Cambridge). Rabbit antiserum to HPV16 L2
Trp-E fusion protein was provided by Dr. Denise Galloway (University of Washington, Seattle).

Amino acid sequence analysis and the antigen index prediction. The antigenic index (AI) (Jameson and Wolf, 1988, Comp. Appl., Biosci 4 181-186) is a measure of the probability that a peptide sequence is antigenic. It is calculated by summing several weighted measures of secondary structure. Values for the predicted HPV16L1 sequence were calculated using PLOTSTRUCTURE software.

In FIGS. 9 and 10, reactivity (OD 415) of the sera in ELISA with a series of overlapping peptides corresponding to the sequence of HPV16 L1 is shown. Peptide numbers corresponding to the HPV16L1 sequence (see Table 1) are indicated.

Figure 11:
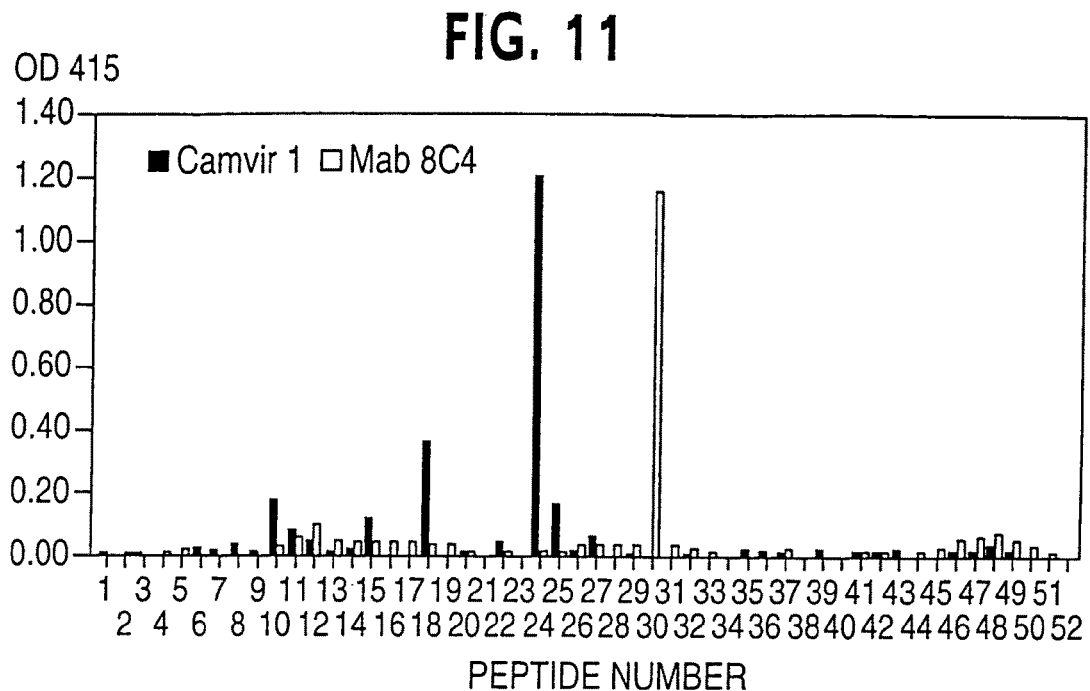
FIG. 11 illustrates reactivity of two MAbs specific for L1 with a series of overlapping peptides of the HPV16 L1 molecule.
Figure 11A:
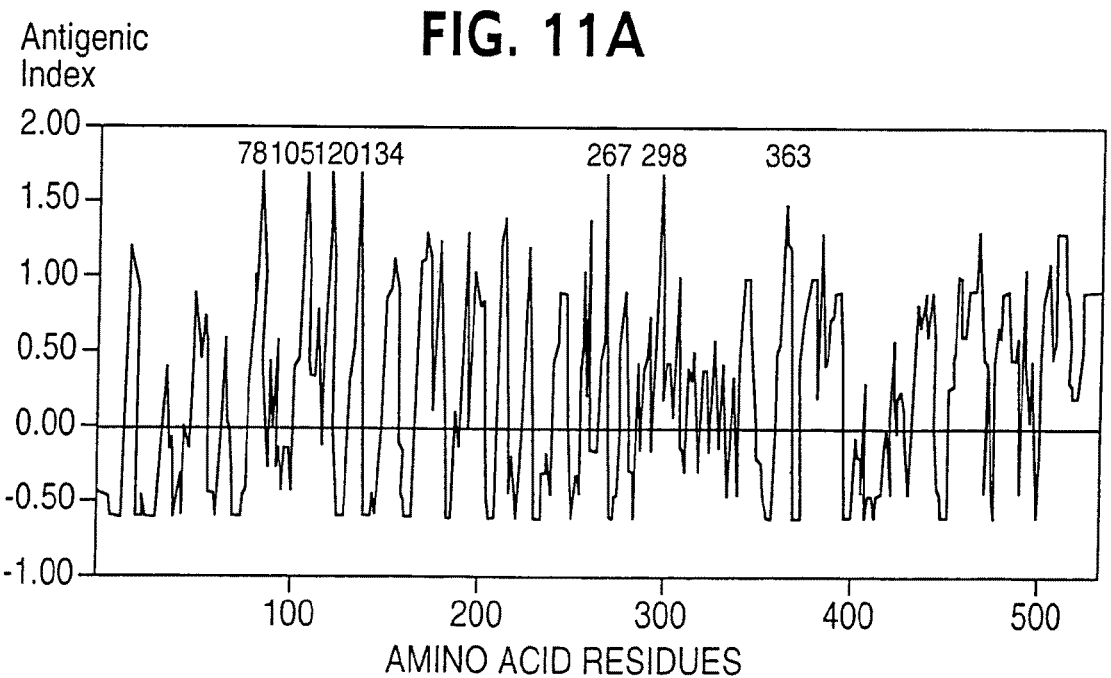
FIG. 11A illustrates antigenic index prediction of HPV16L1.

In FIGS. 11 and 11A, the numbering system for the amino acids correspond to HPV16L1 from the first putative initiation codon. The regions with AI value over 1.5 are indicated.

Figure 12:
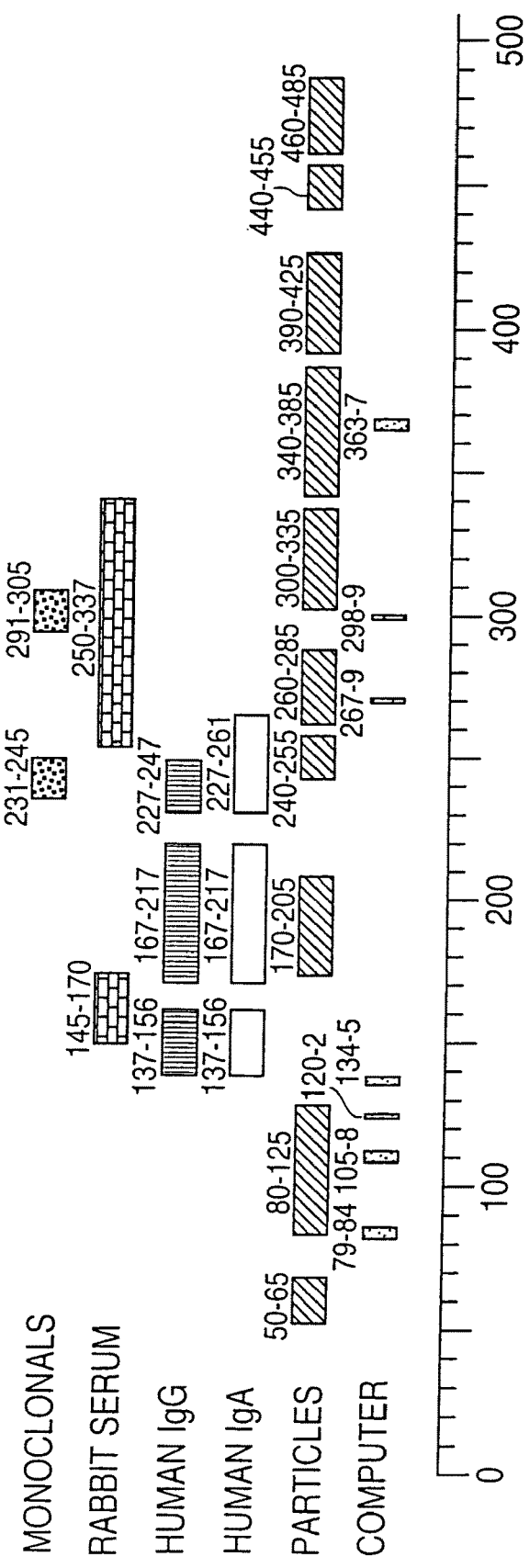
FIG. 12 shows an epitope map of HPV16 L1.

In FIG. 12, the regions of HPV16L1 within which B epitopes have been shown to lie in a range of mapping systems are shown. Results with sera from mice immunized with the VLPs (Particles) and with IgA and IgG antibodies in sera from humans with cervical cancer (Human IgA and Human IgG) (Dillner et al. 1990 Int. J. Cancer 45 529-535) were obtained using overlapping peptides. The murine anti VLP antisera were held to be significantly reactive with a peptide if the OD was greater than 0.55. Results from rabbits immunized with an L1 fusion protein (Rabbit Serum) (Muller et al. 1990 J Gen Virol 71 2709-2717) are plotted: these were determined using a series of partial-length expression clones and the whole length of the sequence within which the epitope(s) lay is shown. Also indicated are the algorithm-predicted B epitopes (Computer) (Jameson and Wolf Comp. Appl. Biosci 4 181-186 1988) and the epitopes recognised by the published anti-HPV16L1 monoclonal antibodies (Monoclonals) (Cason et al. J. Gen Virol. 70 2973-2987 1989; McLean et al. J. Clin Pathol. 43 488-492 1990). The scale shows the position of the epitopes along the 531 aa L1 protein, and is numbered from the N-terminal methionine (residue 1). For each epitope containing peptide, the exact location with regard to the N-terminal methionine is also given.

A series of 15-mer synthetic peptides of the HPV16 L1 protein, covering the whole length of the protein with five aa overlaps, was used to define the epitopes in L1 recognized by the various immune sera. Each of 16 antisera from the three tested inbred mouse strains. BALB/c(H-$2^d$), C57B1/6(H-$2^b$), and B1OA (H-$2^{b/d}$), recognized multiple linear peptides of the L1 protein, and essentially the same peptides from HPV16 L1 were recognized by all strains tested (FIG. 10). Five individual sera were tested from each strain. A peptide was designated reactive if the OD with a serum was greater than the mean+3SD of the ODs of the negative control sera; this gave a cutoff for reactivity of 0.260. Sera from mice immunized with CFA alone had an OD 415 reactivity of less than 0.260 with all the L1 peptides. While some variation was seen in the intensity of the reactivity of each anti-VLP serum from a given strain with each peptide, each of the peptides was reactive (OD>0.260) with either all or none of the anti-VLP sera from each strain of mouse. The isotype of the peptide specific antibody in the anti-VLP sera was examined using IgG- and IgA-specific anti-mouse immunoglobulin antibodies. The IgG response was as shown (FIGS. 9 and 10) and no significant IgA reactivity could be detected to any peptide (OD<0.050). As most peptides were reactive with the anti-VLP sera an arbitrary OD value of five times the mean negative value was used to define major reactive regions of the L1 protein: the major immunoreactive L1 peptides were evenly distributed along the length of the L1 protein, as seven were in the amino terminal third of the molecule, seven in the middle third, and eight in the carboxy terminal third. In contrast, the monoclonal antibodies specific for HPV16 L1 recognized single major linear epitopes as previously described (Cason et al., above, McLean et al, 1990 above). Four of the five reactive anti-HPV16L1 monoclonal antibodies (5A4, ID6, 3D1, 8C4) were reactive with peptide 30 (291-305), whereas Camvir 1 recognized peptide 24 (231-245) (FIG. 11 and ill). Sera from mice immunized with the virus-like particles failed to react with either of these peptides.

An algorithm was used to deduce likely B epitopes of HPV16L1, based on the predicted protein secondary structure. Possible antigenic regions were calculated as an antigenic index (AI) (Jameson and Wolf, 1988, above) on the basis of chain flexibility, high accessibility and high degree of hydrophilicity (FIG. 11). A region with an Al value over 1.5 was regarded as a predicted B epitope. Seven such regions were found (amino acids 79-84, 105-108, 120-122, 134-135, 267, 269, 298-299, 363-367) and five of these seven regions were within the 22 peptides to which major reactivity was seen with antisera from mice immunized with synthetic HPV16 capsids. The summary of the B epitope specificity of antisera from different sources is shown in FIG. 12.

In further consideration of Examples 1-2 it is noted that papilloma viruses generally produce virions in infected keratinocytes which are readily identifiable by electron microscopy (Almeida et al, 1962, J. Invest, Dermatol 38, 337-345) and which in some cases can be purified and shown to be infectious (Rowson and Mahy, 1967, Bacterial. Reo. 31, 110-131). HPV 16 virions are however, not seen in HPV16 infected cervical epithelial tissue although HPV16 L1 and L2 late gene transcription occurs in differentiated genital epithelium (Crum et al, 1988. J. Virol. 62, 84-90) and L1 translation produces immunoreactive L1 protein in these tissues (Stanley et al 1989, Int. J. Cancer 43, 672-676). In this specification we have shown that expression of HPV16 L1 and L2 genes in epithelial cells is both necessary and sufficient to allow assembly of HPV16 virion-like particles and thus the L1 and L2 proteins of HPV 16 are not defective with regard to virion assembly. The expression of HPV16 late genes in tissues appears to be strictly regulated by the epithelial environment (Taichman et al, 1983, J. Invest. Dermatol 1, 137-140). Failure to detect HPV16 virions in vivo, despite transcription of L1 and L2 and translation of L1, suggests that there is either a post transcriptional block to L2 production in cervical epithelium, or an inhibitor of virion assembly. In the HPV16 containing cell line W12, derived from cervical tissue, virus-like particles were observed when the cells underwent terminal differentiation in vivo in a murine microenvironment (Sterling et al 1990. J. Virol 64, 63056307) suggesting that such cells have no block to virion assembly, and that insufficient translation of L2 or other unknown reasons may explain failure to demonstrate HPV16 virions in cervical tissues.

Our EM studies show that the empty HPV16 virion has an average size of about 40 mm which is smaller than other papilloma viruses, but has a similar surface structure compared with other papilloma viruses such as rabbit papilloma virus (Finch and Klug, 1965 J. Mol. Biol. 13 1-12), or human wart virus (Rowson and Mahy 1967 above). Sedimentation showed an empty capsid density of about 1.31 g/ml, the density expected of empty papilloma virus capsid compared with about 1.36 g/ml for intact HPV1a virions (Doorbar and Gallimore, 1987, J. Virol. 61, 2793-2799).

The L1 protein from HPV has potential glycosylation sites, and purified BPV particles have minor electrophoretic forms of L1 whose mobility is sensitive to endoglycosidase treatment (Larsen et al, 1987, J. Virol 61, 3596-3601). L2 from HPV 1a and HPV 11 has been observed to be a doublet (Rose et al, 1990, J. Gen. Virol, 71, 2725-2729; Doorbar and Gallimore, 1987 above; Jin et al, 1989, J. Gen. Virol. 70, 1133-1140) and this has been attributed to differences in glycosylation. Our data show that the L1 protein in HPV16 capsomeres is also glycosylated, and that two different glycosylation states exist.

In this specification we used synthetic virus like particles to study immunogenicity of the HPV16 capsid proteins produced in a eukaryotic system. Capsid proteins produced in eukaryotic cells were used since papilloma-virus capsid proteins produced in eukaryotic cells undergo post-translational modification (Browne et al., 1988 J. Gen. Virol. 69 1263-1273; Zhou et al. 1991 Virology 185 625-632) which may be an important determinant of antigen presentation. A recombinant vaccinia expression vector was chosen because no native HPV16 particles are available from clinical lesions, or from viral propagation in cell culture. We used the HPV16 VLPs to produce polyclonal anti-VLP antisera in mice, and these sera reacted strongly with the HPV16 capsids by ELISA. We have demonstrated by immunoblotting that the anti-VLP antisera recognized epitopes in denatured L1 (FIG. 2) and L2. Moreover, anti-VLP sera defined 22 major reactive peptides in a series of fifty one 15-mer peptides of L1. These data indicate that antisera raised against viral particles nevertheless frequently recognize linear determinants. The profile of humoral reactivity with the set of L1 peptides was almost identical across two MHC disparate mouse strains, suggesting that there are sufficient T epitopes in L1 that MHC restriction is not limiting in determining the humoral response to the HPV16 L1 protein in the mouse strains tested here.

The data for B epitope specificity obtained with our murine anti-VLP antisera can be compared (FIG. 12) with a similar study of "immune" serum from women with cervical dysplasia (Dillner et al., 1990 Int. J Cancer 45 529-535). Several peptides were recognized by both immune human sera and the anti-VLP antisera, but the majority of peptides reactive with the murine anti-VLP antisera were not reactive with the immune human sera (FIG. 12). Neither of the regions of L1 (221-235, 291305) recognized by L1-specific monoclonal antibodies (Cason et al., 1989; McLean et al., 1990) were recognized by our murine anti-VLP antisera. As L1 fusion proteins were used to raise these MAbs, and have also been used to screen for antibody to L1 in human serum, the lack of reactivity of human sera with L1 fusion protein (Jenison et al., 1990 J. Infect. Dis 162 60-69; Söchel et al., 1991 Int. J. Cancer 48 682-688) may be explained by the failure of the L1 fusion proteins to display the epitopes of L1 which are presented to the human immune system by native L1 protein.

Screening for antibodies to the L1 Protein with peptides can detect only linear epitopes. In an attempt to determine whether the reactivity in the murine sera was directed against both linear and conformational determinants we carried out ELISA assays with the particles treated in two ways: one said to preserve native particles and the other to produce denatured protein (Dillner et al., 1991 J. Virol. 65 6862-6871). We did not fine any serum or monoclonal antibody reactive exclusively with particles treated in one or other manner, though one MAB (Camvir 1) reacted more strongly with the denatured that the "native" particles. Lack of reactivity of the majority of the MAbs with the denatured particles suggests that they were only partially denatured, as the same antibodies react with denatured protein in a Western blot. Conversely, the reactivity of Camvir 1 with the native particles is not proof that the linear epitope recognized by this antibody is recognizing denatured L1 protein present in some amount in the native particle preparation, and we have no proof that intact VLPs are preserved under our ELISA conditions.

Since most antibodies recognize conformation dependent determinants (Benjamin et al., 1984 Ann. Rev. Immunol. 2, 67-101), which can involve several noncontiguous polypeptide sequences (Amit et al., 1986 Science 233 747-753), antibodies elicited to virions are unlikely to recognise fused or denatured proteins as well as the native protein, as has been shown for HPV1 antisera (Steele and Gallimore, 1990 Virology 174 388398). Virions of some skin-wart-associated HPV are available in quantities sufficient for serological assays (Almeida and Goffe, 1965 Lancet 2 1205-1207; Kienzler et al., 1983 Br J. Dermatol. 108 665-672; Pfister and Zur Hausen, 1978 Int. J. Cancer 21 161-165; Pyrhsonen et al., 1980 Br. J. Dermatol 102 247-254; Pass and Maizel, 1973 J. Invest. Dermatol 60 307-311) for wart parings. The prevalence of antibodies to purified virions in human immune serum varies from 20 (Genner, 1971 Acta. Derm. Venereol (Stockh) 51 365-373) to 88% (Morison, 1975 Br J Dermatol 93 545-552) depending on the detection system used. However, until recently, virions of the genital HPV types have been unavailable for serological study. The nude mice xenograft system (Kreider et al., 1987 J Virol 61 590-593) has allowed production of HPV11 particles for the detection of human antibodies (Bonnez et al., 1991 J. Gen Virol 72 1343-1347). We anticipate that the HPV16 VLPs described here will allow similar studies of seroreactivity to native HPV16 particles to be developed, and the observed lack of reactivity in human serum to HPV15L1 fusion proteins (Jenison et al., 1991 J Virol 65 1208-1218; Kochel et al., 1991 above) may simply parallel the similar observations with HPV1 (Steele and Gallimore, 1990 Virology 174 388-398).

Antibodies to BPV structural proteins have virus-neutralizing activity (Pilacinski et al., 1986 Ciba Found. Symp. 120 136-156) and antisera raised against purified HPV11 virions could also neutralize infectious HPV11 in an athymic mouse xenograft system (Christensen and Kreider, 1990 J Virol 64 3151-3156). Our results indicated that the purified synthetic HPV16 capsids are immunogenic and could be used to produce and evaluate virus-neutralizing antibodies specific for this oncogenic virus. BPV1 L1 protein expressed in *Escherichia coli* and BPV particles have both protected cattle from development of warts (Pilacinski et al., 1986; Jarrett et al., 1990 Vet. Rec. 126 449-452). A similar immune response to HPV16 virus-like particles would be the basis of a potential vaccine to prevent HPV16-associated cervical cancer.

Figure 13A:
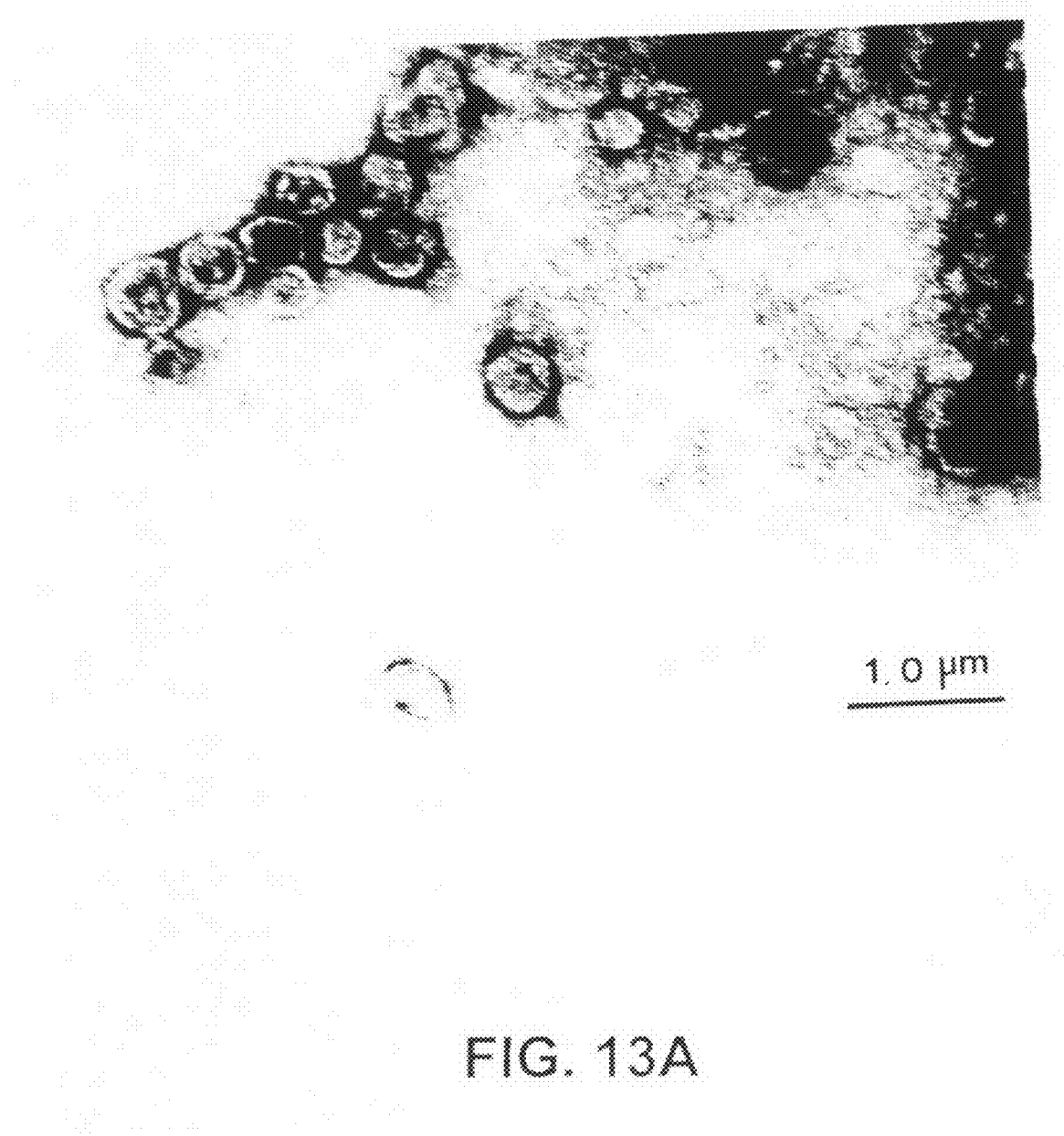
FIG. 13A illustrates synthetic HPV16 VLPs as used for immunisation.
Figure 13B:
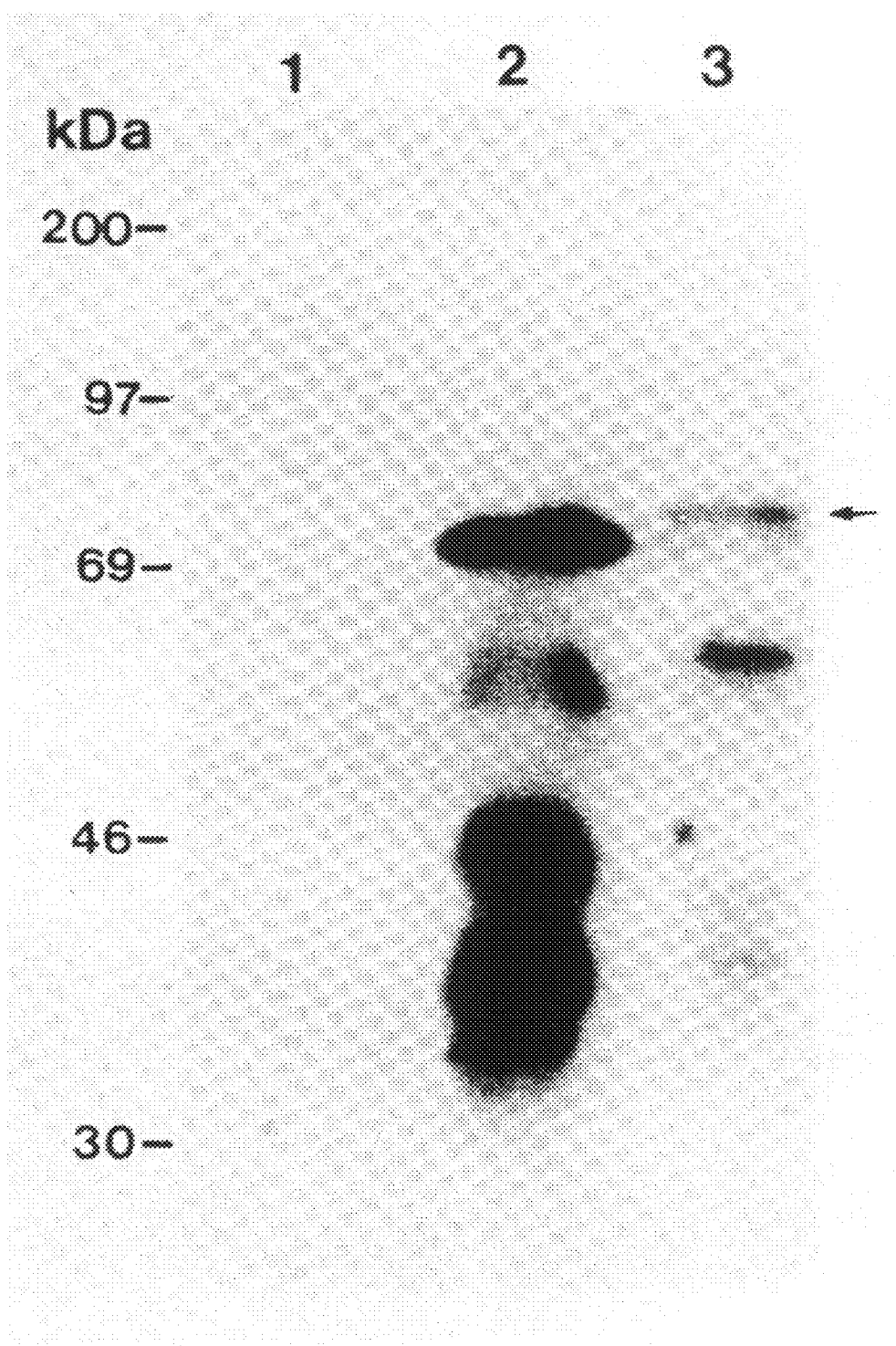
FIG. 13B shows reactivity of the purified VLPs with anti HPV16 L2 antiserum by western blot.

In FIG. 13A, after infection with pLC201VV, CV1 cell lysates were subjected to equilibrium gradient sedimentation. Purified virus-like particles were examined by transmission electron microscopy after negative staining with Phosphotungstic acid. [bar=100 nm].

In FIG. 13B, Lane 1, the lysate from CV1 cells infected with wild type virus; lane 2, lysate from L1 and L2 expressing virus pLC201VV; lane 3, purified virus-like particles. The L2 protein was probed with a rabbit anti HPV16 L2 antibody followed by 125I-protein A. The molecular weights are indicated on the left and L2 bands are arrowed.

Reference may also be made to FIGS. 13A and 13B which show that HPV16 L1 and L2 double recombinant W contain L2 protein as demonstrated by western blot, using purified VLPs and a rabbit antiserum raised against VV recombinant L2 protein.

EXAMPLE 3

BPV1 VLPS

It has also been ascertained that bovine papillomavirus (BPV) 1 virions similarly produced in vitro using W recombinant for the BPV1 capsid proteins can package BPV1 DNA. Complete virions are able to infect a permissible mouse fibroblast cell line, as indicated by transcription of the E1 viral open reading frame, and infection is inhibited by incubation of virions with antibodies to the capsid protein of BPV1. In contrast to the observations for HPV16, virus like particles assemble in cells infected with W recombinant for the BPV1 L1 capsid protein alone, but L2 protein is required to package BPV1 DNA to produce infectious virions.

With reference to the HPV16 VLPs referred to above, these particles appeared to consist of capsomeres typical of those seen in HPV1 and BPV1 particles purified from clinical lesions (Bakar et al, J. C. Biphys J 60 1445-1456-1991, Staquet et al., J. Dermatologica 162 213219, 1981), though the overall morphology of the HPV16 particles was rather different to naturally occurring HPV1 and BPV1 particles. As natural HPV16 virions have not been purified from clinical lesions, it was considered desirable to ascertain whether this morphological difference was a property of HPV16, or the recombinant vaccinia virus (rVV) system used to produce the virions. A series of VVs were therefore made, each doubly recombinant for the L1 and L2 caps id proteins of HPV6, HPV11, and of BPV1. Infection of CV-1 cells with each of these double recombinant VVs produced virus like particles, and these resembled the authentic HPV1 and BPV1 virions more closely than the HPV16 particles. We chose to study the BPV-1 particles, as natural BPV-1 particles are better characterised morphologically and immunologically (Chen et al, Baker et al 1991, Cowsert et al., J. Natl Cancer Inst. 79 1053-1057) and cell lines are available which are permissive for the episomal replication of BPV-1 DNA (Law et al 1981 DNAS 78 27272731).

In this example, BPV1L1 is expressed from the p4b natural vaccinia late promoter and L2 from the p480 synthetic vaccinia late promoter. The *E. coli* gpt gene is used as the selection marker. Flanking sequences are the vaccinia B24k gene, which provides a vaccinia sequence for homologous recombination. The BPV1 L1 and L2 genes were cloned by PCR from plasmid pml-1. Because the BPV1 genome is linearised and cloned into this plasmid at a BamHI site in the BPV1 L2 ORF, the BPV1 genome was first isolated from pml-1 by BamHI digestion and recircularised, and the circularised BPV-1 DNA was used as the PCR template. Oligonucleotide primers used for L1 amplification were:

```
                                            (SEQ ID NO: 57)
    5'-CGGGATCCATGGCGTTGTGGCAACAAGGCCAGAAGCTG.

(SEQ ID NO: 58)
    5' CGGGATCCTTATTTTTTTTTTTTTTTGCAGGCTTACTGG.
```

The BamHI site is underlined and the first methionine and stop codons are in bold.

Oligonucleotide primers for L2 amplification were:

(SEQ ID NO: 59)
5'-GCAGATCTATGTGCACGAAAAAGAGTAAAACGTGCCAGTGC.

(SEQ ID NO: 60)
5' GCAGATCTTTAGGCATGTTTCCGTTTTTTTCGTTTCC.

The BgI II sites are underlined and the first methionine and stop codons are in bold. The amplified 1478 bp L1 fragment was cloned into the BamHI site in plasmid RK19 to produce RK19BPVL1. The L1 gene and vaccinia 4b promoter were isolated from this plasmid by digestion with MluI and SmaI and transferred into plasmid pSX3 to produce pSXBPVL1. The 1409 bp L2 fragment was digested with Bgl II and cloned into the BamHI site in plasmid p480 to produce p480BPVL2. The synthetic vaccinia late promoter and BPV L2 gene were cloned from this plasmid into the Sma1 site in pSXBPVL1 to produce the doubly recombinant plasmid pSXBPVL1L2. Transfection of pSXBPVL1 or pSXBPVL1L2 DNA into monolayers of CV-1 infected with wild type (wt) VV WR strain resulted in the rVVs pSXBPVL1W (L1 expressing) and pSXBPVL1L2VV (L1 and L2 expressing). Recombinant vaccinia viruses were purified three times in presence of mycophenolic acid. Following purification, large-scale preparations of the recombinants were made and used throughout these experiments.

Figure 14A:
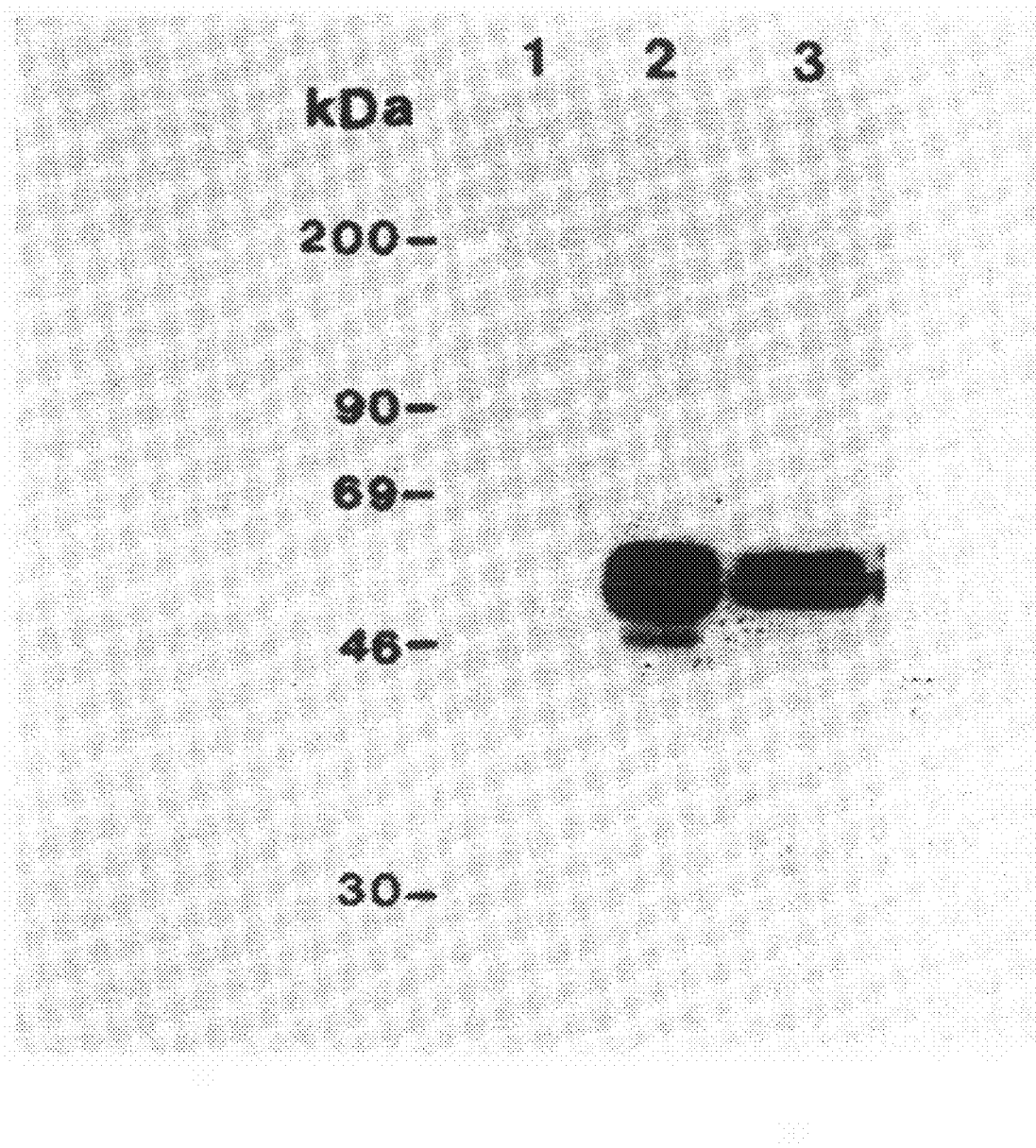
FIGS. 14A and 14B show analysis of BPV1 L1 and L2 expression in CV-1 cells infected with wild type and recombinant vaccinia viruses.

In FIG. 14A there is shown immunoprecipitation analysis of recombinant BPV1 L1 in vaccinia-infected cells. CV-1 cells were infected at 10 pfu/cell with wt vaccinia virus (Lane 1); pSXBPVL1VV (lane 2); pSXBPVL 1L2W (lane 3) and harvested 48 hrs postinfection. BPV1L1 protein was detected with BPV1 specific rabbit antiserum. The 58 kDa L1 protein is indicated by an arrow.

Figure 14B:
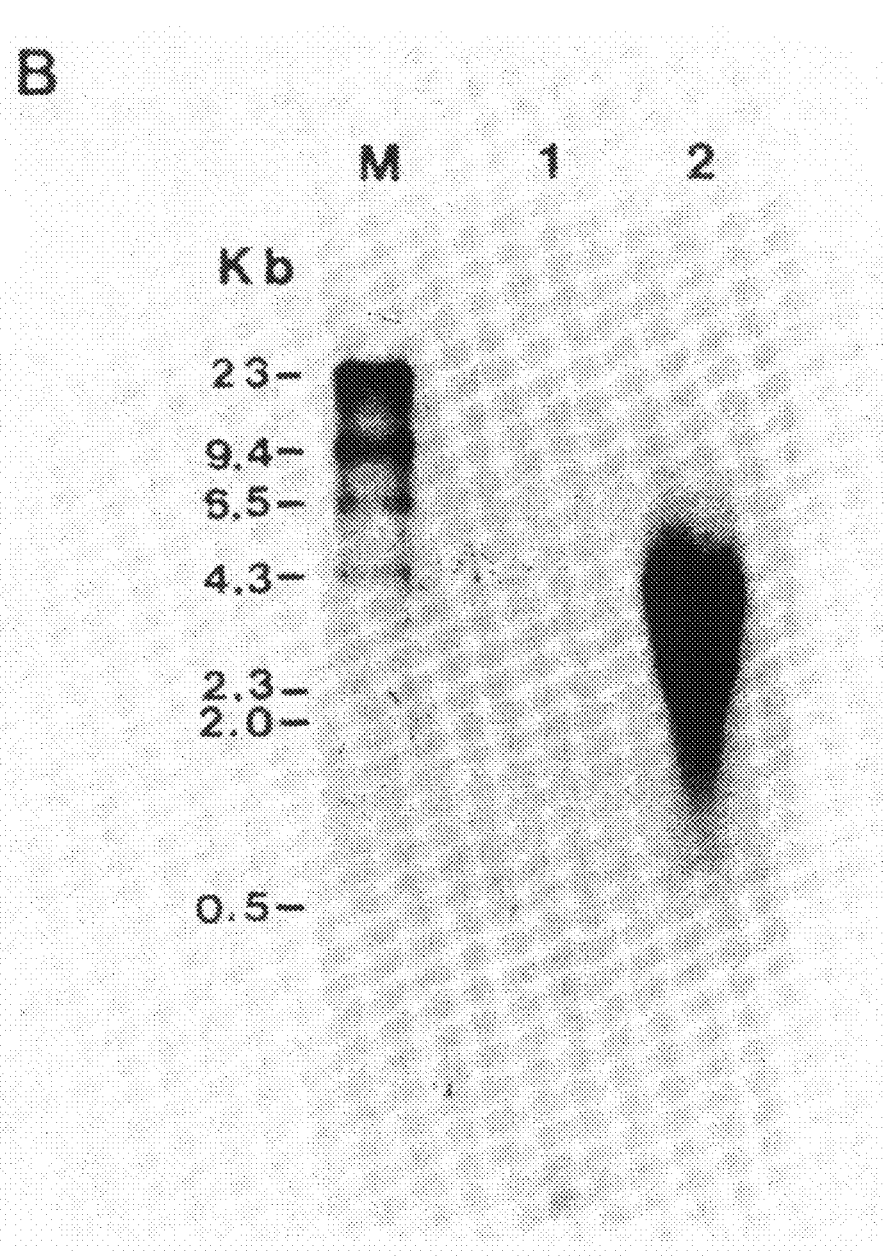

In FIG. 14B there is shown northern blot analysis of BPV1 L2 expression. RNA extracted from CV-1 cells infected with wt W (lane 1); pSXBPVL1L2VV (lane 2) was probed with the BPV1 L2 gene. The variable length of the L2 homologous transcripts is typical of transcripts expressed from W promoters. For immunoprecipitation, cells infected with rws were lysed with RIPA buffer (0.1% SDS, 1% Triton X-100, 1% sodium deoxcholate, 150 mM NaCl, 0.5 g/ml aprotinin, 10 mM Tri.s, pH7.4). Soluble proteins were immunoprecipitated with rabbit anti BPV1 antibody (DAKO, Glostrup) at 1:1000 dilution. Precipitated proteins were collected with protein-A sepharose, separated on 10% SDS polyacrylamide gels and blotted onto nitrocellulose filters. After blocking with skim milk, the filters were exposed to the anti BPV1 serum (1:1000) followed by 1251-protein A (0.1 pCi/ml) and visualised by autoradiography. Total RNA was extracted from cells, and purified by centrifugation through CsCl as described previously. Total RNA, 30 g per track, was run on 1.2% formadelhyde-agarose gels, transferred to nylon membranes, and probed with a 32P-labelled BPV1 L1 gene.

Figure 15A:
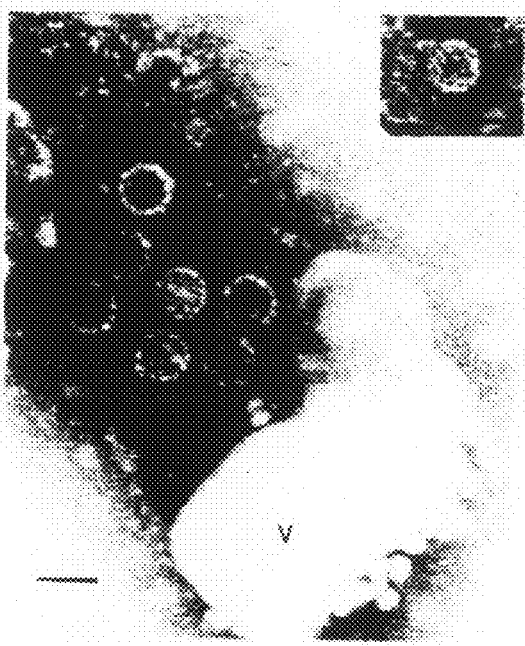
FIGS. 15A and 15B show electron microscopy of BPV1 capsids obtained from cells infected with recombinant vaccinia virus.

In FIG. 15A reference is made to pSXBPVLiL2VV. Some particles from CON/BPV cells infected with pSXBPVL1L2W have electron dense cores (Insert).

Figure 15B:
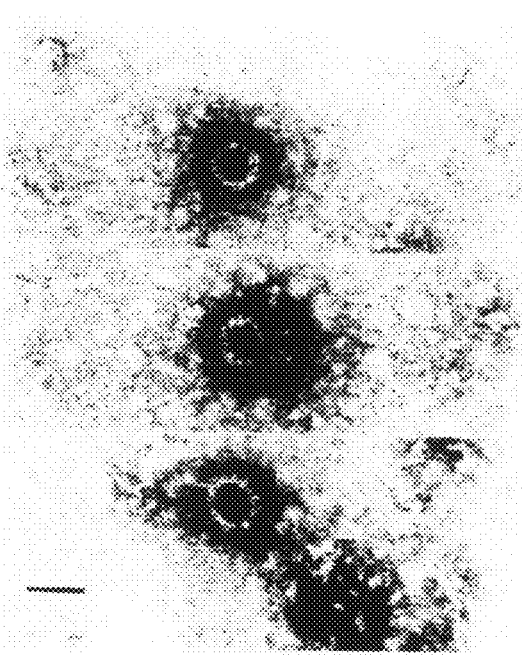

In FIG. 15B reference is made to pSXBPVL1W. A contaminating vaccinia virus in (A) is indicated by a "V". The scale bars represent 50 nm. Cells were harvested two days postinfection, washed with PBS, lysed by freeze and thaw three times and sonicated in PBS. Cell debris was removed by low-speed centrifugation, and the supernants were layered on a 20% (w/v) sucrose cushion and centrifuged for 2 hours at 100,000×g. The pellets were resuspended in PBS and analysed in a JEOL 1200EX electron microscope after negative staining with 1% (w/v) phosphotungstic acid (pH 7.0).

As the ratio of the L1 to L2 proteins in authentic BPV1 particles is approximately 5:1 (Pfister, H. & Fuchs, E. in Papillomaviruses and human disease (eds Syrjanen, K., Gissman, L & Koss, L. G.) Vol. 1-18 (Springer-Verlag, Berlin, 1987), we used a strong natural promoter for the L1 gene and a weak synthetic promoter for the L2 gene for our doubly recombinant VV, and the resulting ratio of L1 mRNA to L2 mRNA on a northern blot from rVV infected CV-1 cells was approximately 10:1. CV-1 cells infected with this rW expressed BPV1 L1 protein (FIG. 14A) and L2 mRNA (FIG. 14B), and large numbers of 50 nm icosahedral virus-like particles of apparently authentic morphology (FIG. 5a) could be purified from the infected cells. Our previous work with HPV16 had shown that both L1 and L2 proteins were required for the assembly of HPV 16 virus-like particles as described above, which contrasts with the observation that, for parvovirus (Rajigaya et al, 1991 DNAS 46464650), bluetongue virus (Loudon et al, 1991 Virology 182, 793-801), and polyoma virus (Salunke et al, 1986, Cell 46, 895-904), virus like particles assemble in cells if the major capsid protein alone is expressed as a recombinant protein. We therefore produced a VV recombinant for BPV1 L1 and observed that when CV-1 cells were infected with this VV, virus like particles of similar morphology to those obtained with the L1 and L2 double recombinant W could be purified (FIG. 15b). Similar empty icosahedral virions were obtained after infection of CV-1 cells with VV recombinant for the L1 proteins of HPV6 or HPV11. The lack of morphologically authentic PV virion in cells infected with the HPV16L1 and L2rW, and the lack of PV virions seen in HPV16 infected tissue by electron microscopy (Schneider (1987) Papillomaviruses and Human Disease Vol 19-39 Springer Verlag Berlin), suggests that HPV16 in contrast to other PVs may be defective with respect to viral capsid formation.

A minority of virus like particles from cells infected with the VPV1 L1/L2 rVV is shown in the FIG. 15a insert.

The cloning strategy for HPV11L1/L2 and HPV6bL1/L2 double expressing recombinant vaccinia viruses is described below:

For HPV11L1:

(SEQ ID NO: 61)
5' CAGATCTCAGATGTGGCGGCCTAGCGACAGCACAGTATATGTGCC (SEQ ID NO: 62)
5' CGGGAATTCGTGTAACAGGACACACATAATAATTGTTTATTGCACAAAA

The PCR product was digested by BgIII/EcoRI and cloned into RK19 under control of 4b promoter. The promoter/11L1 sequence was then cloned into pSX3 BamHl site blunted by Klenow. The resultant plasmid was pSX11L1.

For 11L2

(SEQ ID NO: 63)
5'GCGGATCCATGAAACCTAGGGCACGCAGACGTAAACGTGCG (SEQ ID NO: 64)
5'CGCCCGGGCTAGGCCGCCACATCTGTAAAAAATAAGGG

The Bam/HI/Smal digested PCR fragment was cloned into p480 under synthetic 28 k late promoter. Then the promoter/11L2 fragment was transferred to pSX11Li. The 11L1/L2 double recombinant expressing plasmid was named as pSX1iL1/L2.

For HPV6bll:

(SEQ ID NO: 65)
5'CGCCCGGGTTACCTTTTAGTTTTGGCGCGCTTACGTTTAGG (SEQ ID NO: 66)
5'GCGGATCCAGATGTGGCGGCCTAGFCGACAGCACAGTATATG

The PCR product was cut by BamH1/Sma1 and cloned into RK19 under control of 4b promoter. The promoter/6L1 were then cloned into pSX3 to produce pSX6L1.

For HPV8L2:

The HPV6L2 was isolated from 6b genome by Accl/Xbal (4422-5903). The fragment was blotted by klenow and inserted into p480. The synthetic 28 k promoter plus 6bL2 was cloned into pSX6L1 to form double recombinant plasmid pSX6L1/L2.

Thereafter plasmids pSX11L1 and pSX1iL1/L2 infected a host cell (eg CV1 cells or C127 cells) to produce VV p SX11L1 and VV pSX11 L1/L2 which after transfection of a host cell infected with wild type vaccinia virus formed VLPs containing L1 protein (derived from VV pSX1iL1) and L1 and L2 protein (derived from VV pSX11L1/L2). In similar manner w pSX6L1 and VV pSX6L1/L2 after transfection of a host cell produced VLPs containing HPV6b L1 and VLPs containing HPV6b L1 and HPV6b L2.

It also will be appreciated that the invention includes within its scope viruses doubly recombinant for papillomaviruses capsid proteins L1 and L2 as well as recombinant viruses containing papillomavirus capsid protein L1.

It will further be appreciated that the invention includes within its scope a method of diagnosis of papilloma virus infection by ELISA including the step of detection of VLP particles containing proteins L1 and L2.

TABLE 1

15 AA overlapping peptides from the predicted sequence of the HPV16 L1 protein

| SEQ ID NO. | SEQUENCE | RANGE |
|---|---|---|
| 1 | MQVTFIYILVITCYE | (1-15) |
| 2 | ITCYENDVNVYHIFF | (11-25) |
| 3 | YHIFFQMSLWLPSEA | (21-35) |
| 4 | LPSEATVYLPPVPVS | (31-45) |
| 5 | PVPVSKVVSTDEYVA | (41-55) |
| 6 | DEYVARTNIYYHAGT | (51-65) |
| 7 | YHAGTSRLLAVGHPY | (61-75) |
| 8 | VGHPYFPIKKPNNNK | (71-85) |
| 9 | PNNNKILVPKVSGLQ | (81-95) |
| 10 | VSGLQYRVFRIHLPD | (91-105) |
| 11 | IHLPDPNKFGFPDTS | (101-115) |
| 12 | FPDTSFYNPDTQRLV | (111-125) |
| 13 | TWRLVWACVGVEVGR | (121-135) |
| 14 | VEVGRGQPLGVGISG | (131-145) |
| 15 | VGISGHPLLNKLDDT | (141-155) |
| 16 | KLDDTENASAYAANA | (151-165) |
| 17 | YAANAGVDNRECISM | (161-175) |
| 18 | ECISMDYKQTQLCLI | (171-185) |
| 19 | QLCLIGCKPPIGEHW | (191-195) |
| 20 | IGEHWGKGSPCTNVA | (191-205) |
| 21 | CTNVAVNPGDCPPLE | (101-215) |
| 22 | CPPLELINTVIQDGD | (211-225) |
| 23 | IQDGDMVHTGFGAMD | (221-235) |
| 24 | FGAMDFTTLQANKSE | (231-245) |
| 25 | ANKSEVPLDICTSIC | (241-255) |
| 26 | CTSICKYPDYIKMVS | (251-265) |
| 27 | IKMVSEPYGDSLFFY | (261-275) |
| 28 | SLFFYLRREQMFVRH | (271-285) |
| 29 | MFVRHLFNRAGTVGE | (281-295) |
| 30 | GTVGENVPDDLYIKG | (291-305) |
| 31 | LYIKGSGSTANLASS | (301-315) |
| 32 | NLASSNYFPTPSGSM | (311-325) |
| 33 | PSGSMVTSDAQIFNK | (321-335) |
| 34 | QIFNKPYWLQRAQGH | (331-345) |
| 35 | RAQGHNNGICWGNQL | (341-355) |
| 36 | WGNQLFVTVVDTTRS | (351-365) |
| 37 | DTTRSTNMSLCAAIS | (361-375) |
| 38 | CAAISTSETTYKNTN | (371-385) |
| 39 | YKNTNFKEYLRHGEE | (381-395) |
| 40 | RHGEEYDLQFIFQLC | (391-405) |
| 41 | IFQLCKITLTADVMT | (401-415) |
| 42 | ADVMTYIHSMNSTIL | (411-425) |
| 43 | NSTILEDWNFGLQPP | (421-435) |
| 44 | GLQPPPGGTLEDTYR | (431-445) |
| 45 | EDTYRFVTQAIACQK | (441-455) |
| 46 | IACQKHTPPAPKEDD | (451-465) |
| 47 | PKEDDPLKKYTFWEV | (461-475) |
| 48 | TFWEVNLKEKFSADL | (471-485) |
| 49 | FSADLDQFPLGRKFL | (481-495) |
| 50 | GRKFLLQAGLKAKPK | (491-505) |
| 51 | KAKPKFTLGKRKATP | (501-515) |
| 52 | RKATPTTSSTSTTAK | (511-525) |
| 53 | STTAKRKKRKL | (521-531) |

The sequence of each L1 peptide is give using the single letter code. The location of each peptide within the HPV16 L1 protein is given, assigning position 1 to the N terminal methionine. The short C terminal peptide (no 53) was not used for these experiments.

TABLE 2

Immunoreactivity to virus-like particles of sera from mice immunized with synthetic HPV16 capsids.

| | Reactivity with virus-like particles | | |
|---|---|---|---|
| | Mice immunized with VLPs | | Immunised with |
| Mouse strain | Expt 1 (n = 5) | Expt 2 (n = 5) nn2 | CFA |
| BALB/C | 1.06 ± 1.29* | 1.71 ± 0.06 | 0.36 ± 0.04 |
| B10A | 1.08 ± 0.06 | 1.75 ± 0.04 | 0.24 ± 0.02 |
| C57B1/6 | 0.86 ± 0.20 | 1.70 ± 0.12 | 0.25 ± 0.03 |

*Values are OD 415 units, and are given as the mean ± 1 standard deviation

What is claimed is:

1. An isolated HPV-16 L1 protein encoded by a polynucleotide in which the first methionine codon of said polynucleotide corresponds to the second ATG codon of an HPV-16 L1 gene, wherein said HPV-16 L1 protein is capable of forming a virus-like particle when expressed with HPV-16 L2 protein.

2. An immunogenic composition that comprises the HPV-16 L1 protein of claim 1.

3. The immunogenic composition of claim 2, further comprising an adjuvant.

4. A virus-like particle that comprises the HPV-16 L1 protein of claim 1.

5. An immunogenic composition that comprises the virus-like particle of claim 4.

6. The immunogenic composition of claim 5, further comprising an adjuvant.

7. An isolated HPV-16 L1 protein encoded by a 1518 base pair polynucleotide in which the first methionine codon of said polynucleotide corresponds to the second ATG codon of an HPV-16 L1 gene, wherein said HPV-16 L1 protein is capable of forming a virus-like particle when expressed with HPV-16 L2 protein.

8. An immunogenic composition that comprises the HPV-16 L1 protein of claim 7.

9. The immunogenic composition of claim 8, further comprising an adjuvant.

10. A virus-like particle that comprises the HPV-16 L1 protein of claim 7.

11. An immunogenic composition that comprises the virus-like particle of claim 10.

12. The immunogenic composition of claim 11, further comprising an adjuvant.

13. An isolated HPV-16 L1 protein encoded by a polynucleotide consisting essentially of a polynucleotide segment that begins at nucleotide 5637 of the HPV16 genome, wherein said HPV-16 L1 protein lacks the N-terminal amino acid sequence encoded by nucleotides 5559 to 5636 of the HPV-16 genome and is capable of forming a virus-like particle when expressed with HPV-16 L2 protein.

14. An immunogenic composition that comprises the HPV-16 L1 protein of claim 13.

15. The immunogenic composition of claim 14, further comprising an adjuvant.

16. A virus-like particle that comprises the HPV-16 L1 protein of claim 13.

17. An immunogenic composition that comprises the virus-like particle of claim 16.

18. The immunogenic composition of claim 17, further comprising an adjuvant.

19. An isolated HPV-16 L1 protein that has the N-terminal amino acid sequence MSLWLPSEA (amino acid residues 7-15 of SEQ ID NO: 3) or SLWLPSEA (amino acid residues 8-15 of SEQ ID NO: 3), wherein said HPV-16 L1 protein is capable of forming a virus-like particle when expressed with HPV-16 L2 protein.

20. An immunogenic composition that comprises the HPV-16 L1 protein of claim 19.

21. The immunogenic composition of claim 20, further comprising an adjuvant.

22. A virus-like particle that comprises the HPV-16 L1 protein of claim 19.

23. An immunogenic composition that comprises the virus-like particle of claim 22.

24. The immunogenic composition of claim 23, further comprising an adjuvant.

25. An isolated HPV-16 L1 protein that lacks the N-terminal amino acid sequence encoded by nucleotides 5559 to 5636 of the HPV-16 genome, wherein said HPV-16 L1 protein is capable of forming a virus-like particle when expressed with HPV-16 L2 protein.

26. An immunogenic composition that comprises the HPV-16 L1 protein of claim 25.

27. The immunogenic composition of claim 26, further comprising an adjuvant.

28. A virus-like particle that comprises the HPV-16 L1 protein of claim 25.

29. An immunogenic composition that comprises the virus-like particle of claim 28.

30. The immunogenic composition of claim 29, further comprising an adjuvant.

\* \* \* \* \*

SEQUENCE LISTING

```
<160> NUMBER OF SEQ ID NOS: 66

<210> SEQ ID NO 1
<211> LENGTH: 15
<212> TYPE: PRT
<213> ORGANISM: Human papillomavirus type 16

<400> SEQUENCE: 1

Met Gln Val Thr Phe Ile Tyr Ile Leu Val Ile Thr Cys Tyr Glu
 1               5                  10                  15

<210> SEQ ID NO 2
<211> LENGTH: 15
<212> TYPE: PRT
<213> ORGANISM: Human papillomavirus type 16

<400> SEQUENCE: 2

Ile Thr Cys Tyr Glu Asn Asp Val Asn Val Tyr His Ile Phe Phe
 1               5                  10                  15

<210> SEQ ID NO 3
<211> LENGTH: 15
<212> TYPE: PRT
<213> ORGANISM: Human papillomavirus type 16

<400> SEQUENCE: 3

Tyr His Ile Phe Phe Gln Met Ser Leu Trp Leu Pro Ser Glu Ala
 1               5                  10                  15

<210> SEQ ID NO 4
<211> LENGTH: 15
<212> TYPE: PRT
<213> ORGANISM: Human papillomavirus type 16

<400> SEQUENCE: 4

Leu Pro Ser Glu Ala Thr Val Tyr Leu Pro Pro Val Pro Val Ser
 1               5                  10                  15

<210> SEQ ID NO 5
<211> LENGTH: 15
<212> TYPE: PRT
<213> ORGANISM: Human papillomavirus type 16
```

-continued

```
<400> SEQUENCE: 5

Pro Val Pro Val Ser Lys Val Val Ser Thr Asp Glu Tyr Val Ala
 1               5                  10                  15

<210> SEQ ID NO 6
<211> LENGTH: 15
<212> TYPE: PRT
<213> ORGANISM: Human papillomavirus type 16

<400> SEQUENCE: 6

Asp Glu Tyr Val Ala Arg Thr Asn Ile Tyr Tyr His Ala Gly Thr
 1               5                  10                  15

<210> SEQ ID NO 7
<211> LENGTH: 15
<212> TYPE: PRT
<213> ORGANISM: Human papillomavirus type 16

<400> SEQUENCE: 7

Tyr His Ala Gly Thr Ser Arg Leu Leu Ala Val Gly His Pro Tyr
 1               5                  10                  15

<210> SEQ ID NO 8
<211> LENGTH: 15
<212> TYPE: PRT
<213> ORGANISM: Human papillomavirus type 16

<400> SEQUENCE: 8

Val Gly His Pro Tyr Phe Pro Ile Lys Lys Pro Asn Asn Asn Lys
 1               5                  10                  15

<210> SEQ ID NO 9
<211> LENGTH: 15
<212> TYPE: PRT
<213> ORGANISM: Human papillomavirus type 16

<400> SEQUENCE: 9

Pro Asn Asn Asn Lys Ile Leu Val Pro Lys Val Ser Gly Leu Gln
 1               5                  10                  15

<210> SEQ ID NO 10
<211> LENGTH: 15
<212> TYPE: PRT
<213> ORGANISM: Human papillomavirus type 16

<400> SEQUENCE: 10

Val Ser Gly Leu Gln Tyr Arg Val Phe Arg Ile His Leu Pro Asp
 1               5                  10                  15

<210> SEQ ID NO 11
<211> LENGTH: 15
<212> TYPE: PRT
<213> ORGANISM: Human papillomavirus type 16

<400> SEQUENCE: 11

Ile His Leu Pro Asp Pro Asn Lys Phe Gly Phe Pro Asp Thr Ser
 1               5                  10                  15

<210> SEQ ID NO 12
<211> LENGTH: 15
<212> TYPE: PRT
<213> ORGANISM: Human papillomavirus type 16
```

```
<400> SEQUENCE: 12

Phe Pro Asp Thr Ser Phe Tyr Asn Pro Asp Thr Gln Arg Leu Val
  1               5                  10                  15

<210> SEQ ID NO 13
<211> LENGTH: 15
<212> TYPE: PRT
<213> ORGANISM: Human papillomavirus type 16

<400> SEQUENCE: 13

Thr Gln Arg Leu Val Trp Ala Cys Val Gly Val Glu Val Gly Arg
  1               5                  10                  15

<210> SEQ ID NO 14
<211> LENGTH: 15
<212> TYPE: PRT
<213> ORGANISM: Human papillomavirus type 16

<400> SEQUENCE: 14

Val Glu Val Gly Arg Gly Gln Pro Leu Gly Val Gly Ile Ser Gly
  1               5                  10                  15

<210> SEQ ID NO 15
<211> LENGTH: 15
<212> TYPE: PRT
<213> ORGANISM: Human papillomavirus type 16

<400> SEQUENCE: 15

Val Gly Ile Ser Gly His Pro Leu Leu Asn Lys Leu Asp Asp Thr
  1               5                  10                  15

<210> SEQ ID NO 16
<211> LENGTH: 15
<212> TYPE: PRT
<213> ORGANISM: Human papillomavirus type 16

<400> SEQUENCE: 16

Lys Leu Asp Asp Thr Glu Asn Ala Ser Ala Tyr Ala Ala Asn Ala
  1               5                  10                  15

<210> SEQ ID NO 17
<211> LENGTH: 15
<212> TYPE: PRT
<213> ORGANISM: Human papillomavirus type 16

<400> SEQUENCE: 17

Tyr Ala Ala Asn Ala Gly Val Asp Asn Arg Glu Cys Ile Ser Met
  1               5                  10                  15

<210> SEQ ID NO 18
<211> LENGTH: 15
<212> TYPE: PRT
<213> ORGANISM: Human papillomavirus type 16

<400> SEQUENCE: 18

Glu Cys Ile Ser Met Asp Tyr Lys Gln Thr Gln Leu Cys Leu Ile
  1               5                  10                  15

<210> SEQ ID NO 19
<211> LENGTH: 15
<212> TYPE: PRT
<213> ORGANISM: Human papillomavirus type 16
```

-continued

```
<400> SEQUENCE: 19

Gln Leu Cys Leu Ile Gly Cys Lys Pro Pro Ile Gly Glu His Trp
1               5                   10                  15

<210> SEQ ID NO 20
<211> LENGTH: 15
<212> TYPE: PRT
<213> ORGANISM: Human papillomavirus type 16

<400> SEQUENCE: 20

Ile Gly Glu His Trp Gly Lys Gly Ser Pro Cys Thr Asn Val Ala
1               5                   10                  15

<210> SEQ ID NO 21
<211> LENGTH: 15
<212> TYPE: PRT
<213> ORGANISM: Human papillomavirus type 16

<400> SEQUENCE: 21

Cys Thr Asn Val Ala Val Asn Pro Gly Asp Cys Pro Pro Leu Glu
1               5                   10                  15

<210> SEQ ID NO 22
<211> LENGTH: 15
<212> TYPE: PRT
<213> ORGANISM: Human papillomavirus type 16

<400> SEQUENCE: 22

Cys Pro Pro Leu Glu Leu Ile Asn Thr Val Ile Gln Asp Gly Asp
1               5                   10                  15

<210> SEQ ID NO 23
<211> LENGTH: 15
<212> TYPE: PRT
<213> ORGANISM: Human papillomavirus type 16

<400> SEQUENCE: 23

Ile Gln Asp Gly Asp Met Val His Thr Gly Phe Gly Ala Met Asp
1               5                   10                  15

<210> SEQ ID NO 24
<211> LENGTH: 15
<212> TYPE: PRT
<213> ORGANISM: Human papillomavirus type 16

<400> SEQUENCE: 24

Phe Gly Ala Met Asp Phe Thr Thr Leu Gln Ala Asn Lys Ser Glu
1               5                   10                  15

<210> SEQ ID NO 25
<211> LENGTH: 15
<212> TYPE: PRT
<213> ORGANISM: Human papillomavirus type 16

<400> SEQUENCE: 25

Ala Asn Lys Ser Glu Val Pro Leu Asp Ile Cys Thr Ser Ile Cys
1               5                   10                  15

<210> SEQ ID NO 26
<211> LENGTH: 15
<212> TYPE: PRT
<213> ORGANISM: Human papillomavirus type 16
```

```
<400> SEQUENCE: 26

Cys Thr Ser Ile Cys Lys Tyr Pro Asp Tyr Ile Lys Met Val Ser
 1               5                  10                  15

<210> SEQ ID NO 27
<211> LENGTH: 15
<212> TYPE: PRT
<213> ORGANISM: Human papillomavirus type 16

<400> SEQUENCE: 27

Ile Lys Met Val Ser Glu Pro Tyr Gly Asp Ser Leu Phe Phe Tyr
 1               5                  10                  15

<210> SEQ ID NO 28
<211> LENGTH: 15
<212> TYPE: PRT
<213> ORGANISM: Human papillomavirus type 16

<400> SEQUENCE: 28

Ser Leu Phe Phe Tyr Leu Arg Arg Glu Gln Met Phe Val Arg His
 1               5                  10                  15

<210> SEQ ID NO 29
<211> LENGTH: 15
<212> TYPE: PRT
<213> ORGANISM: Human papillomavirus type 16

<400> SEQUENCE: 29

Met Phe Val Arg His Leu Phe Asn Arg Ala Gly Thr Val Gly Glu
 1               5                  10                  15

<210> SEQ ID NO 30
<211> LENGTH: 15
<212> TYPE: PRT
<213> ORGANISM: Human papillomavirus type 16

<400> SEQUENCE: 30

Gly Thr Val Gly Glu Asn Val Pro Asp Asp Leu Tyr Ile Lys Gly
 1               5                  10                  15

<210> SEQ ID NO 31
<211> LENGTH: 15
<212> TYPE: PRT
<213> ORGANISM: Human papillomavirus type 16

<400> SEQUENCE: 31

Leu Tyr Ile Lys Gly Ser Gly Ser Thr Ala Asn Leu Ala Ser Ser
 1               5                  10                  15

<210> SEQ ID NO 32
<211> LENGTH: 15
<212> TYPE: PRT
<213> ORGANISM: Human papillomavirus type 16

<400> SEQUENCE: 32

Asn Leu Ala Ser Ser Asn Tyr Phe Pro Thr Pro Ser Gly Ser Met
 1               5                  10                  15

<210> SEQ ID NO 33
<211> LENGTH: 15
<212> TYPE: PRT
<213> ORGANISM: Human papillomavirus type 16
```

-continued

```
<400> SEQUENCE: 33

Pro Ser Gly Ser Met Val Thr Ser Asp Ala Gln Ile Phe Asn Lys
 1               5                  10                  15

<210> SEQ ID NO 34
<211> LENGTH: 15
<212> TYPE: PRT
<213> ORGANISM: Human papillomavirus type 16

<400> SEQUENCE: 34

Gln Ile Phe Asn Lys Pro Tyr Trp Leu Gln Arg Ala Gln Gly His
 1               5                  10                  15

<210> SEQ ID NO 35
<211> LENGTH: 15
<212> TYPE: PRT
<213> ORGANISM: Human papillomavirus type 16

<400> SEQUENCE: 35

Arg Ala Gln Gly His Asn Asn Gly Ile Cys Trp Gly Asn Gln Leu
 1               5                  10                  15

<210> SEQ ID NO 36
<211> LENGTH: 15
<212> TYPE: PRT
<213> ORGANISM: Human papillomavirus type 16

<400> SEQUENCE: 36

Trp Gly Asn Gln Leu Phe Val Thr Val Val Asp Thr Thr Arg Ser
 1               5                  10                  15

<210> SEQ ID NO 37
<211> LENGTH: 15
<212> TYPE: PRT
<213> ORGANISM: Human papillomavirus type 16

<400> SEQUENCE: 37

Asp Thr Thr Arg Ser Thr Asn Met Ser Leu Cys Ala Ala Ile Ser
 1               5                  10                  15

<210> SEQ ID NO 38
<211> LENGTH: 15
<212> TYPE: PRT
<213> ORGANISM: Human papillomavirus type 16

<400> SEQUENCE: 38

Cys Ala Ala Ile Ser Thr Ser Glu Thr Thr Tyr Lys Asn Thr Asn
 1               5                  10                  15

<210> SEQ ID NO 39
<211> LENGTH: 15
<212> TYPE: PRT
<213> ORGANISM: Human papillomavirus type 16

<400> SEQUENCE: 39

Tyr Lys Asn Thr Asn Phe Lys Glu Tyr Leu Arg His Gly Glu Glu
 1               5                  10                  15

<210> SEQ ID NO 40
<211> LENGTH: 15
<212> TYPE: PRT
<213> ORGANISM: Human papillomavirus type 16
```

-continued

<400> SEQUENCE: 40

Arg His Gly Glu Glu Tyr Asp Leu Gln Phe Ile Phe Gln Leu Cys
 1               5                  10                  15

<210> SEQ ID NO 41
<211> LENGTH: 15
<212> TYPE: PRT
<213> ORGANISM: Human papillomavirus type 16

<400> SEQUENCE: 41

Ile Phe Gln Leu Cys Lys Ile Thr Leu Thr Ala Asp Val Met Thr
 1               5                  10                  15

<210> SEQ ID NO 42
<211> LENGTH: 15
<212> TYPE: PRT
<213> ORGANISM: Human papillomavirus type 16

<400> SEQUENCE: 42

Ala Asp Val Met Thr Tyr Ile His Ser Met Asn Ser Thr Ile Leu
 1               5                  10                  15

<210> SEQ ID NO 43
<211> LENGTH: 15
<212> TYPE: PRT
<213> ORGANISM: Human papillomavirus type 16

<400> SEQUENCE: 43

Asn Ser Thr Ile Leu Glu Asp Trp Asn Phe Gly Leu Gln Pro Pro
 1               5                  10                  15

<210> SEQ ID NO 44
<211> LENGTH: 15
<212> TYPE: PRT
<213> ORGANISM: Human papillomavirus type 16

<400> SEQUENCE: 44

Gly Leu Gln Pro Pro Gly Gly Thr Leu Glu Asp Thr Tyr Arg
 1               5                  10                  15

<210> SEQ ID NO 45
<211> LENGTH: 15
<212> TYPE: PRT
<213> ORGANISM: Human papillomavirus type 16

<400> SEQUENCE: 45

Glu Asp Thr Tyr Arg Phe Val Thr Gln Ala Ile Ala Cys Gln Lys
 1               5                  10                  15

<210> SEQ ID NO 46
<211> LENGTH: 15
<212> TYPE: PRT
<213> ORGANISM: Human papillomavirus type 16

<400> SEQUENCE: 46

Ile Ala Cys Gln Lys His Thr Pro Pro Ala Pro Lys Glu Asp Asp
 1               5                  10                  15

<210> SEQ ID NO 47
<211> LENGTH: 15
<212> TYPE: PRT
<213> ORGANISM: Human papillomavirus type 16

-continued

```
<400> SEQUENCE: 47

Pro Lys Glu Asp Asp Pro Leu Lys Lys Tyr Thr Phe Trp Glu Val
 1               5                  10                  15

<210> SEQ ID NO 48
<211> LENGTH: 15
<212> TYPE: PRT
<213> ORGANISM: Human papillomavirus type 16

<400> SEQUENCE: 48

Thr Phe Trp Glu Val Asn Leu Lys Glu Lys Phe Ser Ala Asp Leu
 1               5                  10                  15

<210> SEQ ID NO 49
<211> LENGTH: 15
<212> TYPE: PRT
<213> ORGANISM: Human papillomavirus type 16

<400> SEQUENCE: 49

Phe Ser Ala Asp Leu Asp Gln Phe Pro Leu Gly Arg Lys Phe Leu
 1               5                  10                  15

<210> SEQ ID NO 50
<211> LENGTH: 15
<212> TYPE: PRT
<213> ORGANISM: Human papillomavirus type 16

<400> SEQUENCE: 50

Gly Arg Lys Phe Leu Leu Gln Ala Gly Leu Lys Ala Lys Pro Lys
 1               5                  10                  15

<210> SEQ ID NO 51
<211> LENGTH: 15
<212> TYPE: PRT
<213> ORGANISM: Human papillomavirus type 16

<400> SEQUENCE: 51

Lys Ala Lys Pro Lys Phe Thr Leu Gly Lys Arg Lys Ala Thr Pro
 1               5                  10                  15

<210> SEQ ID NO 52
<211> LENGTH: 15
<212> TYPE: PRT
<213> ORGANISM: Human papillomavirus type 16

<400> SEQUENCE: 52

Arg Lys Ala Thr Pro Thr Thr Ser Ser Thr Ser Thr Thr Ala Lys
 1               5                  10                  15

<210> SEQ ID NO 53
<211> LENGTH: 11
<212> TYPE: PRT
<213> ORGANISM: Human papillomavirus type 16

<400> SEQUENCE: 53

Ser Thr Thr Ala Lys Arg Lys Lys Arg Lys Leu
 1               5                  10

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 54
cagatctatg tctctttggc tgcctagtga ggcc                         34

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 55
cagatcttta cagcttacgt tttttgcgtt tagc                         34

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Promoter
      sequence

<400> SEQUENCE: 56
gagctctttt tttttttttt tttttttggca tataaatgga ggtaccc           47

<210> SEQ ID NO 57
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 57
cgggatccat ggcgttgtgg caacaaggcc agaagctg                     38

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 58
cgggatcctt atttttttt ttttttgca ggcttactgg                     40

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 59
gcagatctat gagtgcacga aaagagtaa aacgtgccag tgc                43

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 60
gcagatcttt aggcatgttt ccgttttttt cgtttcc                      37
```

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
cagatctcag atgtggcggc ctagcgacag cacagtatat gtgcc        45

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
cggaattcgt gtaacaggac acacataata attgtttatt gcacaaaa        48

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
gcggatccat gaaacctagg gcacgcagac gtaaacgtgc g        41

<210> SEQ ID NO 64
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
cgcccgggct aggccgccac atctgtaaaa aataaggg        38

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
cgcccgggtt accttttagt tttggcgcgc ttacgtttag g        41

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
gcggatccag atgtggcggc ctagcgacag cacagtatat g        41